(12) United States Patent
Leiber

(10) Patent No.: US 6,956,005 B2
(45) Date of Patent: Oct. 18, 2005

(54) USE OF TELLURIUM IN CARBON-SUPPORTED, NOBLE METAL-CONTAINING CATALYSTS FOR LIQUID PHASE OXIDATION REACTIONS

(75) Inventor: Mark A. Leiber, St. Peters, MO (US)

(73) Assignee: Monsanto Technology LLC, St. Louis, MO (US)

( * ) Notice: Subject to any disclaimer, the term of this patent is extended or adjusted under 35 U.S.C. 154(b) by 28 days.

(21) Appl. No.: 10/610,359

(22) Filed: Jun. 30, 2003

(65) Prior Publication Data

US 2004/0068138 A1 Apr. 8, 2004

Related U.S. Application Data

(60) Provisional application No. 60/392,529, filed on Jun. 28, 2002.

(51) Int. Cl.$^7$ ............ B01J 21/18; B01J 23/00; B01J 23/42; B01J 23/16; C07F 9/22
(52) U.S. Cl. ............ 502/185; 502/182; 502/325; 502/334; 502/353; 562/17
(58) Field of Search ................. 502/182, 185, 502/325, 353, 334; 562/17

(56) References Cited

U.S. PATENT DOCUMENTS

| | | | |
|---|---|---|---|
| 3,799,758 A | 3/1974 | Franz | |
| 3,950,402 A | 4/1976 | Franz | |
| 3,969,398 A | 7/1976 | Hershman | |
| 4,026,950 A | 5/1977 | Le Ludec | |
| 4,225,727 A | 9/1980 | Kamiyama et al. | |
| 4,351,962 A | 9/1982 | Gradeff et al. | |
| 4,582,650 A | 4/1986 | Felthouse | |
| 4,624,937 A | 11/1986 | Chou | |
| 4,696,772 A | 9/1987 | Chou | |
| 5,091,561 A | 2/1992 | Riley et al. | |
| 5,179,228 A | 1/1993 | Martin Ramon et al. | |
| 5,292,936 A | 3/1994 | Franczyk | |
| 5,500,485 A | 3/1996 | Hodgkinson | |
| 5,606,107 A | 2/1997 | Smith | |
| 5,739,390 A | 4/1998 | Franczyk et al. | |
| 5,783,737 A | 7/1998 | Metivier | |
| 6,278,017 B1 * | 8/2001 | Stern et al. | 562/17 |
| 6,417,133 B1 | 7/2002 | Ebner et al. | |
| 6,586,621 B2 | 7/2003 | Leiber et al. | |
| 2001/0002424 A1 | 5/2001 | Siebenhaar et al. | |
| 2003/0171611 A1 * | 9/2003 | Leiber | 562/17 |

FOREIGN PATENT DOCUMENTS

| | | |
|---|---|---|
| DE | 196 00 741 A1 | 7/1996 |
| EP | 1 067 108 A2 | 1/2001 |
| GB | 1 468 109 | 3/1977 |
| GB | 1 601 715 | 11/1981 |
| WO | WO 99/03402 A1 | 1/1999 |
| WO | WO 99/43430 A1 | 9/1999 |
| WO | WO 00/01707 A1 | 1/2000 |
| WO | WO 00/09517 A2 | 2/2000 |
| WO | WO 01/07447 A1 | 2/2001 |
| WO | WO 01/46208 A2 | 6/2001 |
| WO | WO 01/92272 A2 | 12/2001 |

OTHER PUBLICATIONS

Cameron, D. S. et al., "Carbons as Supports for Precious Metal Catalysis", *Catalysis Today*, vol. 7, No. 2, pp. 113–137, Apr. 10, 1990, Elsevier Science Publishers B.V., Amsterdam, The Netherlands.

Franz, John E. et al., "Methods of Preparing Glyphosphate", *Glyphosphate: A Unique Global Herbicide*, Chapter 8, pp. 233–262, 1997, American Chemical Society, Washington, DC, no month.

Mallat, T. et al., "Preparation of Promoted Platinum Catalysts of Designed Geometry and the Role of Promoters in the Liquid–Phase Oxidation of 1–Methoxy–2–Propanol", *Journal of Catalysis*, 1993, pp. 237–253, no month.

Mallat, T. et al., "Oxidation of Alcohols With Molecular Oxygen on Platinum Metal Catalysts in Aqueous Solutions", *Catalysis Today 19*, pp. 247–284, 1994, Elsevier Science B.V., Zürich, Switzerland, no month.

Ponec, Vladimir et al., "Supported Metal Catalysts", *Catalysis by Metals and Alloys*, vol. 95, Chapter 7, pp. 320–356, 1995, Elsevier Science B.V., Amsterdam, The Netherlands, no month.

International Search Report for International Application No. PCT/US03/20497 dated Oct. 24, 2003.

* cited by examiner

*Primary Examiner*—Mark L. Bell
*Assistant Examiner*—Patricia L. Hailey
(74) *Attorney, Agent, or Firm*—Senniger Powers; Joseph Schaper

(57) ABSTRACT

An improved catalyst comprising a noble metal and tellurium at the surface of a carbon support is provided. Also provided are novel methods for preparing such catalysts and novel processes for the use of such catalysts in liquid phase oxidation reactions, particularly the oxidation of N-(phosphonomethyl)iminodiacetic acid or a salt thereof.

100 Claims, No Drawings

USE OF TELLURIUM IN CARBON-SUPPORTED, NOBLE METAL-CONTAINING CATALYSTS FOR LIQUID PHASE OXIDATION REACTIONS

CROSS-REFERENCE TO RELATED APPLICATIONS

This application claims the benefit of U.S. Provisional Application Ser. No. 60/392,529, filed Jun. 28, 2002, the entire disclosure of which is incorporated herein by reference.

FIELD OF THE INVENTION

The present invention relates generally to tellurium-promoted, noble metal-containing catalysts and their use in liquid phase oxidation reactions. More particularly, the invention relates to enhancing the activity, selectivity and/or stability of a carbon-supported, noble metal-containing catalyst by incorporating tellurium as a promoter metal at a surface of the carbon support. In certain preferred embodiments, the tellurium-promoted catalysts of the present invention are used in the liquid phase oxidation of N-(phosphonomethyl)iminodiacetic acid substrates, formaldehyde and/or formic acid.

BACKGROUND OF THE INVENTION

N-(phosphonomethyl)glycine (also known in the agricultural chemical industry as glyphosate) and its salts are conveniently applied as a component of aqueous, post-emergent herbicide formulations. As such, they are particularly useful as a highly effective and commercially important broad-spectrum herbicide for killing or controlling the growth of a wide variety of plants, including germinating seeds, emerging seedlings, maturing and established woody and herbaceous vegetation and aquatic plants.

One of the more widely accepted methods of making N-(phosphonomethyl)glycine comprises the liquid phase oxidative cleavage of a carboxymethyl substituent from an N-(phosphonomethyl)iminodiacetic acid substrate using an oxygen-containing gas in the presence of a heterogeneous oxidation catalyst. As used herein, "N-(phosphonomethyl) iminodiacetic acid substrates" include N-(phosphonomethyl)iminodiacetic acid and salts thereof, wherein the salt-forming cation is, for example, ammonium, alkylammonium, an alkali metal or an alkaline earth metal. N-(phosphonomethyl)glycine may be prepared by the liquid phase oxidative cleavage of N-(phosphonomethyl) iminodiacetic acid with oxygen in accordance with the following reaction:

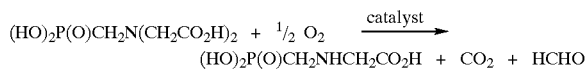

$(HO)_2P(O)CH_2N(CH_2CO_2H)_2 + \frac{1}{2} O_2 \xrightarrow{catalyst} (HO)_2P(O)CH_2NHCH_2CO_2H + CO_2 + HCHO$ Other by-products also may form, such as formic acid, which is formed by oxidation of the formaldehyde by-product and aminomethylphosphonic acid (AMPA), which is formed by oxidation of N-(phosphonomethyl) glycine. The preference for heterogenous catalysis stems, at least in part, from the relative ease with which a particulate heterogeneous catalyst can normally be separated from the reaction product mixture for reuse following the oxidation. The literature is replete with examples of heterogeneous catalysts. See generally, Franz, et al., *Glyphosate: A Unique Global Herbicide* (ACS Monograph 189, 1997) at pp. 233–62 (and references cited therein); Franz, U.S. Pat. No. 3,950,402; Hershman, U.S. Pat. No. 3,969,398; Felthouse, U.S. Pat. No. 4,582,650; Chou, U.S. Pat. Nos. 4,624,937 and 4,696,772; Ramon et al., U.S. Pat. No. 5,179,228; Ebner et al., U.S. Pat. No. 6,417,133; and Leiber et al., U.S. Pat. No. 6,586,621.

A high concentration of formaldehyde in the reaction product mixture resulting from the oxidative cleavage of an N-(phosphonomethyl)iminodiacetic acid substrate is undesirable. In particular, the formaldehyde by-product is undesirable because it tends to react with the N-(phosphonomethyl)glycine product to produce further unwanted by-products including N-methyl-N-(phosphonomethyl)glycine (NMG), which reduces N-(phosphonomethyl)glycine yield. In addition, the formaldehyde by-product itself is undesirable because of its potential toxicity. See Smith, U.S. Pat. No. 5,606,107.

Franz, U.S. Pat. No. 3,950,402, discloses oxidizing the formaldehyde by-product to carbon dioxide and water simultaneously with the oxidative cleavage of the N-(phosphonomethyl)iminodiacetic acid substrate by using a heterogenous oxidation catalyst comprising a noble metal deposited on a carbon support. Such noble metal on carbon oxidation catalysts are referred to as "bifunctional" as the carbon component provides the primary adsorption site for the oxidation of the N-(phosphonomethyl)iminodiacetic acid substrate to form the N-(phosphonomethyl)glycine product and formaldehyde, while the noble metal component provides the primary adsorption site for the oxidation of formaldehyde and formic acid to form carbon dioxide and water. The noble metal component may also tend to reduce the rate of deactivation of the catalyst (i.e., prolong the useful life of the catalyst). The overall reaction is summarized as follows:

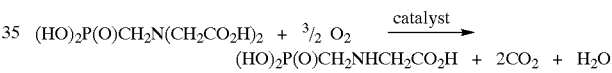

$(HO)_2P(O)CH_2N(CH_2CO_2H)_2 + \frac{3}{2} O_2 \xrightarrow{catalyst} (HO)_2P(O)CH_2NHCH_2CO_2H + 2CO_2 + H_2O$ However, under typical conditions of the oxidation reaction, some of the noble metal in the catalyst used by Franz is oxidized into a more soluble form and both the N-(phosphonomethyl)iminodiacetic acid and N-(phosphonomethyl)glycine product act as chelating ligands that tend to solubilize the noble metal. Thus, even though the process disclosed by Franz produces an acceptable yield and purity of N-(phosphonomethyl)glycine, high losses of the costly noble metal by dissolution into the aqueous reaction solution (i.e., leaching) undermine the economic feasibility of the process.

Ramon et al., U.S. Pat. No. 5,179,228, disclose a process for the preparation of N-(phosphonomethyl)glycine by oxidation of N-(phosphonomethyl)iminodiacetic acid using an oxygen-containing gas in the presence of a noble metal on an activated carbon catalyst. Recognizing the problem of leaching attendant the use of a noble metal on carbon catalyst in the oxidation of an N-(phosphonomethyl) iminodiacetic acid substrate (noble metal losses as great as 30% are reported), Ramon et al. propose flushing the reaction mixture with nitrogen gas under pressure after the oxidation reaction is complete. According to Ramon et al., nitrogen flushing causes redeposition of solubilized noble metal onto the surface of the carbon support and reduces the noble metal loss to less than 1%. However, the amount of noble metal loss incurred with this method is still unacceptable. In addition, re-depositing the noble metal can lead to a loss of noble metal surface area which, in turn, decreases the activity of the catalyst.

Using a different approach, Felthouse, U.S. Pat. No. 4,582,650, discloses using two catalysts: (i) an activated carbon to effect the oxidation of N-(phosphonomethyl) iminodiacetic acid into N-(phosphonomethyl)glycine; and (ii) a co-catalyst to concurrently effect the oxidation of formaldehyde into carbon dioxide and water. The co-catalyst consists of an aluminosilicate support having a noble metal located within its pores. The pores are sized to exclude N-(phosphonomethyl)glycine and thereby prevent the noble metal of the co-catalyst from being poisoned by N-(phosphonomethyl)glycine. According to Felthouse, use of these two catalysts together allows for the simultaneous oxidation of N-(phosphonomethyl)iminodiacetic acid to N-(phosphonomethyl)glycine and of formaldehyde to carbon dioxide and water. This approach, however, suffers from several disadvantages: (1) it is difficult to recover the costly noble metal from the aluminosilicate support for re-use; (2) it is difficult to design the two catalysts so that the rates between them are matched; and (3) the carbon support, which has no noble metal deposited on its surface, tends to deactivate at a rate which can exceed 10% per cycle.

More recently, attention has focused on developing bifunctional noble metal on carbon oxidation catalysts which resist noble metal leaching (i.e., exhibit improved compositional stability) and provide increased activity and/or selectivity, particularly with respect to oxidation of formaldehyde into carbon dioxide and water (i.e., increased formaldehyde activity). Ebner et al., U.S. Pat. No. 6,417,133, disclose "deeply reduced" noble metal on carbon catalysts containing various metal promoters for use in the oxidative cleavage of an N-(phosphonomethyl) iminodiacetic acid substrate and oxidation of other oxidizable reagents and methods for their preparation. Such deeply reduced catalysts exhibit remarkable resistance to noble metal leaching in aqueous, acidic, oxidation reaction media. As a result, the catalyst disclosed by Ebner et al. provides for substantially quantitative oxidation of N-(phosphonomethyl)iminodiacetic acid substrates to N-(phosphonomethyl)glycine products, while maintaining effective oxidation of the formaldehyde and formic acid by-products of the reaction for a prolonged period and/or over numerous oxidation cycles. Still, the process of Ebner et al. typically does not eliminate all the formaldehyde and formic acid by-product and, consequently, also does not eliminate all the NMG. Accordingly, a need persists for improvements which might further reduce noble metal losses, provide increased catalyst stability, activity and/or selectivity, particularly in the oxidation of formaldehyde and other N-(phosphonomethyl)iminodiacetic acid substrate oxidation by-products, and generally extend the useful life of such catalysts.

Tellurium has been described as a promoter metal for use in liquid phase oxidation reactions. For example, in WO 00/01707, Siebenhaar et al. describe oxidizing salts of N-(phosphonomethyl)iminodiacetic acid in the presence of a noble metal on carbon catalyst containing 0.5% to 10% of a doping metal based on the weight of the carbon support. Although the disclosure includes tellurium in a list of potential doping metals, the principal teaching of the reference is directed to the use of commercially prepared noble metal on carbon catalysts doped with bismuth or lead.

SUMMARY OF THE INVENTION

Among certain objects of the present invention, therefore, are the provision of an improved tellurium-promoted, oxidation catalyst comprising tellurium and a noble metal at a surface of a carbon support that exhibits enhanced selectivity, activity or stability in oxidation reactions, particularly the oxidation of an N-(phosphonomethyl) iminodiacetic acid substrate to produce an N-(phosphonomethyl)glycine product and the oxidation of formaldehyde and formic acid by-products to carbon dioxide and water; the provision of processes for preparing such oxidation catalysts so that the catalyst prepared exhibits acceptable compositional stability and prolonged activity, particularly in liquid phase oxidation reactions; and the provision of processes for utilizing such catalysts in liquid phase oxidation reactions, particularly the oxidation of an N-(phosphonomethyl)iminodiacetic acid substrate to produce an N-(phosphonomethyl)glycine product.

Briefly, therefore, a certain embodiment of the present invention is directed to an oxidation catalyst comprising platinum and tellurium at a surface of a carbon support where tellurium constitutes from about 0.02% to about 0.175% by weight of the catalyst.

Another embodiment of the present invention is directed to a catalyst comprising a noble metal and at least two promoter metals at a surface of a carbon support. One of the promoter metals of the catalyst is tellurium and the other promoter metal is selected from the group consisting of iron, bismuth, tin, cadmium, magnesium, manganese, nickel, aluminum, cobalt, lead, titanium, antimony, selenium, rhenium, zinc, cerium, zirconium and germanium.

In another embodiment, the present invention is directed to a catalyst composition comprising tellurium deposited over a noble metal/promoter metal alloy at a surface of a carbon support. The promoter metal comprises a metal selected from the group consisting of iron, bismuth, tin, cadmium, magnesium, manganese, nickel, aluminum, cobalt, lead, titanium, antimony, selenium, rhenium, zinc, cerium, zirconium and germanium.

In a further embodiment, the present invention is directed to a process for preparing a tellurium-promoted, noble metal oxidation catalyst. The process comprises combining an oxidation catalyst precursor comprising a noble metal at a surface of a carbon support with a source of tellurium in a liquid medium to form an oxidation catalyst precursor slurry. An oxygen-containing gas is introduced into the catalyst precursor slurry and tellurium is deposited on a surface of the oxidation catalyst precursor. The process is further characterized in that the temperature of the catalyst precursor slurry during introduction of the oxygen-containing gas is no greater than about 50° C.

Still further, another embodiment of the present invention is directed to a process for preparing a tellurium-promoted, noble metal oxidation catalyst. The process comprises contacting an oxidation catalyst precursor comprising a noble metal at a surface of a carbon support with a source of tellurium and $Fe_2O_3$ in a liquid medium to deposit tellurium on a surface of the catalyst precursor.

A further embodiment of the present invention is directed to a process for preparing a tellurium-promoted, noble metal oxidation catalyst. The process comprises depositing tellurium over a noble metal/promoter metal alloy at a surface of a carbon support wherein the promoter metal is selected from the group consisting of iron, bismuth, tin, cadmium, magnesium, manganese, nickel, aluminum, cobalt, lead, titanium, antimony, selenium, rhenium, zinc, cerium, zirconium and germanium.

In another embodiment, the present invention is directed to a process for oxidizing a substrate selected from the group consisting of N-(phosphonomethyl)iminodiacetic acid or a salt thereof, formaldehyde and formic acid. The process comprises contacting the substrate with an oxidizing agent in the presence of an oxidation catalyst comprising a noble metal and tellurium at a surface of a carbon support, wherein the tellurium constitutes from about 0.02% to about 0.175% by weight of the catalyst.

In another embodiment, the present invention is directed to a process for oxidizing a substrate selected from the group consisting of N-(phosphonomethyl)iminodiacetic acid or a salt thereof, formaldehyde and formic acid. The process comprises contacting the substrate with an oxidizing agent in the presence of an oxidation catalyst comprising a noble metal and at least two promoter metals at a surface of a carbon support. One of the promoter metals of the catalyst is tellurium and the other promoter metal is selected from the group consisting of iron, bismuth, tin, cadmium, magnesium, manganese, nickel, aluminum, cobalt, lead, titanium, antimony, selenium, rhenium, zinc, cerium, zirconium and germanium.

In a further embodiment, the present invention is directed to a process for oxidizing a substrate selected from the group consisting of N-(phosphonomethyl)iminodiacetic acid or a salt thereof, formaldehyde and formic acid. The process comprises contacting the substrate with an oxidizing agent in the presence of an oxidation catalyst. The catalyst comprises tellurium deposited over a noble metal/promoter metal alloy at a surface of a carbon support and the promoter metal is selected from the group consisting of iron, bismuth, tin, cadmium, magnesium, manganese, nickel, aluminum, cobalt, lead, titanium, antimony, selenium, rhenium, zinc, cerium, zirconium and germanium.

In a still further embodiment, the present invention is directed to a process for oxidizing N-(phosphonomethyl) iminodiacetic acid in a liquid reaction medium. The process comprises contacting the liquid reaction medium containing N-(phosphonomethyl)iminodiacetic acid with an oxidizing agent in the presence of an oxidation catalyst comprising a noble metal and tellurium at a surface of a carbon support wherein the tellurium constitutes at least about 0.05% by weight of the catalyst.

Other objects and features of this invention will be in part apparent and in part pointed out hereinafter.

DETAILED DESCRIPTION OF THE PREFERRED EMBODIMENTS

In accordance with the present invention, it has been discovered that tellurium, particularly a relatively modest amount of tellurium, acts as an effective catalyst promoter when incorporated on the surface of carbon-supported, noble metal-containing oxidation catalysts used in liquid phase oxidation reactions. As defined herein, a "promoter" is a metal that tends to increase catalyst selectivity, activity and/or stability. A promoter may also reduce noble metal leaching from the noble metal on carbon catalyst. Further, the present invention provides effective means for depositing tellurium at the surface of a noble metal on carbon catalyst precursor to prepare a stable, tellurium-promoted, oxidation catalyst.

A. The Oxidation Catalyst

The catalyst of the present invention generally comprises tellurium and a noble metal at a surface of a carbon support.

The carbon supports useful in the practice of the present invention are well known in the art and are described, for example, by Ebner et al., U.S. Pat. No. 6,417,133 and Leiber et al., U.S. Pat. No. 6,586,621, which are incorporated herein by reference. In particular, activated, non-graphitized carbon supports are preferred. These supports are characterized by high adsorptive capacity for gases, vapors and colloidal solids and relatively high specific surface areas. The support suitably may be a carbon, char, or charcoal produced by means known in the art, for example, by the destructive distillation of wood, peat, lignite, coal, nut shells, bones, vegetable, or other natural or synthetic carbonaceous matter, but preferably is "activated" to develop adsorptive power. Activation usually is achieved by heating to high temperatures (e.g., from about 800° to about 900° C.) with steam or with carbon dioxide which brings about a porous particle structure and increased specific surface area. In some cases, hygroscopic substances, such as zinc chloride and/or phosphoric acid or sodium sulfate, are added before the destructive distillation or activation, to increase adsorptive capacity. Preferably, the carbon content of the carbon support ranges from about 10% for bone charcoal to about 98% for some wood chars and nearly 100% for activated carbons derived from organic polymers. The non-carbonaceous matter in commercially available activated carbon materials normally will vary depending on such factors as precursor origin, processing and activation method. Many commercially available carbon supports contain small amounts of metals. Carbon supports having the fewest oxygen-containing functional groups at their surfaces are most preferred.

The form of the carbon support is not critical. In one embodiment of this invention, the support is a monolithic support. Suitable monolithic supports may have a wide variety of shapes. Such a support may be, for example, in the form of a screen or honeycomb. Such a support may also, for example, form part of the reactor structure (e.g., an impeller or baffle) in which the liquid phase oxidation is conducted.

In a particularly preferred embodiment, the support is in the form of particulates. Because particulate supports are especially preferred, most of the following discussion focuses on embodiments which use a particulate support. It should be recognized, however, that this invention is not limited to the use of particulate supports.

Suitable particulate supports may have a wide variety of shapes. For example, such supports may be in the form of pellets, granules and powders. Pellet supports typically have a particle size of from about 1 mm to about 10 mm. Preferably, the support is in the form of a powder. These particulate supports may be used in a reactor system as free particles suspended in the liquid reaction medium, or, alternatively, may be bound to a suitable structure in the reactor system, such as a baffle, screen or an impeller.

Typically, a support which is in particulate form comprises a broad size distribution of particles. For powders, preferably at least about 95% of the particles are from about 2 to about 300 $\mu$m in their largest dimension, more preferably at least about 98% of the particles are from about 2 to about 200 $\mu$m in their largest dimension, and most preferably about 99% of the particles are from about 2 to about 150 $\mu$m in their largest dimension with about 95% of the particles being from about 3 to about 100 $\mu$m in their largest dimension. Particles greater than about 200 $\mu$m in their largest dimension tend to fracture into super-fine particles (i.e., less than 2 $\mu$m in their largest dimension), which are difficult to recover.

The specific surface area of the carbon support, measured by the Brunauer-Emmett-Teller (BET) method using $N_2$, is preferably from about 10 to about 3,000 $m^2/g$ (surface area of carbon support per gram of carbon support), more preferably from about 500 to about 2,100 $m^2/g$, and still more preferably from about 750 to about 2,100 $m^2/g$. In some embodiments, the most preferred specific surface area is from about 750 to about 1,750 $m^2/g$.

Carbon supports for use in the present invention are commercially available from a number of sources. The following is a listing of some of the activated carbons which may be used in the practice of the present invention: Darco G-60 Spec and Darco X (ICI-America, Wilmington, Del.); Norit SG Extra, Norit EN4, Norit EXW, Norit A, Norit Ultra-C, Norit ACX, and Norit 4×14 mesh (Amer. Norit Co., Inc., Jacksonville, Fla.); Gl-9615, VG-8408, VG-8590, NB-9377, XZ, NW, and JV (Barnebey-Cheney, Columbus, Ohio); BL Pulv., PWA Pulv., Calgon C 450, and PCB Fines (Pittsburgh Activated Carbon, Div. of Calgon Corporation, Pittsburgh, Pa.); P-100 (No. Amer. Carbon, Inc., Columbus, Ohio); Nuchar CN, Nuchar C-1000 N, Nuchar C-190 A, Nuchar C-115 A, and Nuchar SA-30 (Westvaco Corp., Carbon Department, Covington, Va.); Code 1551 (Baker and Adamson, Division of Allied Amer. Norit Co., Inc., Jacksonville, Fla.); Grade 235, Grade 337, Grade 517, and Grade 256 (Witco Chemical Corp., Activated Carbon Div., New York, N.Y.); and Columbia SXAC (Union Carbide New York, N.Y.).

The catalyst has one or more noble metals at its surface. Preferably, the noble metal is selected from the group consisting of platinum (Pt), palladium (Pd), ruthenium (Ru), rhodium (Rh), iridium (Ir), silver (Ag), osmium (Os), gold (Au) and combinations thereof. In general, platinum is most preferred. Because platinum is presently the most preferred noble metal, the following discussion will be directed primarily to embodiments using platinum. It should be understood, however, that the same discussion is generally applicable to the other noble metals and combinations thereof. It also should be understood that the term "noble metal" as used herein is meant to include the noble metal in its elemental state as well as the noble metal in any of its various oxidation states.

The concentration of the noble metal deposited at the surface of the carbon support may vary within wide limits. Preferably, the noble metal is deposited at the support surface in a concentration of from about 0.5% to about 20% by weight of the catalyst (i.e., [mass of noble metal÷total mass of catalyst]×100%), more preferably from about 2.5% to about 10% by weight of the catalyst, and most preferably from about 3% to about 7.5% by weight of the catalyst. For example, in accordance with a preferred embodiment, the catalyst comprises from about 3% to about 7.5% by weight platinum, and especially about 5% by weight platinum, at the surface of the carbon support. In embodiments wherein the catalyst is intended to catalyze the oxidation of an N-(phosphonomethyl)iminodiacetic acid substrate, noble metal concentrations less than about 0.5% by weight of the catalyst tend to significantly reduce formaldehyde oxidation rate and, as a result, increase NMG production, thereby reducing the N-(phosphonomethyl)glycine product yield. On the other hand, at noble metal concentrations greater than about 20% by weight of the catalyst, layers and clumps of noble metal tend to form. Thus, there are fewer surface noble metal atoms per total amount of noble metal used. This tends to reduce the activity of the catalyst and is an uneconomical use of the costly noble metal.

The dispersion of the noble metal at the surface of the carbon support preferably is such that the concentration of surface noble metal atoms is from about 10 to about 400 μmole/g (μmole of surface noble metal atoms per gram of catalyst), more preferably, from about 10 to about 150 μmole/g, and most preferably from about 15 to about 100 μmole/g. This may be determined, for example, by measuring chemisorption of $H_2$ or CO using a Micromeritics ASAP 2010C (Micromeritics, Norcross, Ga.) or an Altamira AMI100 (Zeton Altamira, Pittsburgh, Pa.).

Preferably, the noble metal is at the surface of the carbon support in the form of metal particles. At least about 90% (number density) of the noble metal particles at the surface of the carbon support are preferably from about 0.5 to about 35 nm in their largest dimension, more preferably from about 1 to about 20 nm in their largest dimension, and most preferably from about 1.5 to about 10 nm in their largest dimension. In a particularly preferred embodiment, at least about 80% of the noble metal particles at the surface of the carbon support are from about 1 to about 15 nm in their largest dimension, more preferably from about 1.5 to about 10 nm in their largest dimension, and most preferably from about 1.5 to about 7 nm in their largest dimension. If the noble metal particles are too small, there tends to be an increased amount of leaching when the catalyst is used in an environment that tends to solubilize noble metals, as is the case when oxidizing an N-(phosphonomethyl)iminodiacetic acid substrate to form an N-(phosphonomethyl)glycine product. On the other hand, as the particle size increases, there tends to be fewer noble metal atoms at the surface per total amount of noble metal used. As discussed above, this tends to reduce the activity of the catalyst and is uneconomical.

In accordance with the present invention, the amount of tellurium at the surface of the carbon support (whether associated with the carbon surface itself, other metal, or a combination thereof) generally constitutes less of the overall catalyst composition as compared to conventional practice, for example, as taught by Siebenhaar et al. in WO 00/01707. The weight percentage of tellurium is typically from about 0.02% to about 0.25% by weight of the catalyst (i.e., [mass of tellurium÷total mass of the catalyst]×100%). In applications wherein the catalyst is utilized in the liquid phase oxidation of an N-(phosphonomethyl)iminodiacetic acid substrate, it is important to note that catalysts containing higher amounts of tellurium are generally less preferred. As discussed in greater detail below, experience to date suggests that higher amounts of tellurium may diminish the rate of the primary reaction (i.e., the oxidative cleavage of a carboxymethyl substituent from an N-(phosphonomethyl)iminodiacetic acid substrate) to a level which renders the process impractical. Thus, for such applications, tellurium preferably constitutes from about 0.02% to about 0.175% by weight of the catalyst, more preferably from about 0.02% to about 0.125% by weight of the catalyst, even more preferably from about 0.02% to about 0.1% by weight of the catalyst, still more preferably from about 0.02% to about 0.08% by weight of the catalyst, and especially from about 0.04% to about 0.08% by weight of the catalyst. For example, in accordance with an especially preferred embodiment, tellurium at the surface of the carbon support constitutes about 0.075% by weight of the catalyst.

In certain embodiments of the present invention, the oxidation catalyst comprises tellurium and one or more other promoter metals in addition to the noble metal at the surface of the carbon support. The promoter metal may, for example, be an additional noble metal at the surface of the carbon support. For example, depending on the application, ruthenium and palladium may act as promoter metals on a catalyst comprising platinum deposited at a carbon support surface. Alternatively, the promoter metal may be, for example, selected from the group consisting of iron (Fe), bismuth (Bi), tin (Sn), cadmium (Cd), magnesium (Mg), manganese (Mn), nickel (Ni), aluminum (Al), cobalt (Co), lead (Pb), titanium (Ti), antimony (Sb), selenium (Se), rhenium (Re), zinc (Zn), cerium (Ce), zirconium (Zr), germanium (Ge) and mixtures thereof.

Tellurium and any other promoter metal(s) may be present at the surface of the carbon support in their elemental state as well as in any of their various oxidation states. Preferably, the tellurium and any other promoter metal(s) are more easily oxidized than the noble metal. In instances where the promoter metal is a noble metal as well, the promoter metal noble metal preferably is more easily oxidized than the non-promoter noble metal. A promoter metal is "more easily oxidized" if it has a lower first ionization potential than the noble metal. First ionization potentials for the elements are widely known in the art and may be found, for example, in the *CRC Handbook of Chemistry and Physics* (CRC Press, Inc., Boca Raton, Fla.).

The amount of the promoter metal other than tellurium at the surface of the carbon support (whether associated with the carbon surface itself, other metal, or a combination thereof) may vary within wide limits depending on, for example, the noble metals and promoter metal(s) employed. Typically, when tellurium is combined with one or more promoter metals at the surface of the catalyst, the other promoter metal(s) is present in an amount of at least about 0.05% by weight of the catalyst (i.e., [mass of promoter metal÷total mass of the catalyst]×100%). Preferably, the other promoter metal constitutes from about 0.05% to about 10% by weight of the catalyst, more preferably from about 0.1% to about 10% by weight of the catalyst. Still more preferably, the other promoter metal at the surface of the carbon support constitutes from about 0.1% to about 2% by weight of the catalyst and especially from about 0.2% to about 1.5% by weight of the catalyst. Generally, promoter metal concentrations of less than about 0.05% by weight do not provide beneficial effects (e.g., increased catalyst activity or selectivity) over an extended period of time. On the other hand, amounts greater than about 10% by weight tend to degrade the activity of the catalyst.

In a preferred embodiment, particularly in applications where the oxidation catalyst is utilized in the liquid phase oxidation of an N-(phosphonomethyl)iminodiacetic acid substrate, formaldehyde and/or formic acid, the catalyst comprises platinum, tellurium and iron at the surface of the carbon support. Iron promoted catalysts are preferred in such applications because they tend to exhibit the greatest activity and stability with respect to formaldehyde and formic acid oxidation. In such embodiments, it is preferred that platinum constitutes from about 0.5% to about 20% by weight of the catalyst, tellurium constitutes from about 0.02% to about 0.175%, more preferably from about 0.02% to about 0.125% by weight of the catalyst and iron constitutes from about 0.1% to about 1.5% by weight of the catalyst. More preferably, platinum constitutes from about 3% to about 7.5% by weight of the catalyst, tellurium constitutes from about 0.02% to about 0.1%, even more preferably from about 0.02% to about 0.08%, still more preferably from about 0.04% to about 0.08% by weight of the catalyst and iron constitutes from about 0.25% to about 1% by weight of the catalyst. For example, in accordance with an especially preferred embodiment, platinum constitutes about 5% by weight of the catalyst, tellurium constitutes about 0.075% by weight of the catalyst and iron constitutes about 0.5% by weight of the catalyst.

B. Preparation of the Oxidation Catalyst

The oxidation catalyst of the present invention may be prepared by depositing tellurium over an oxidation catalyst precursor comprising a noble metal at the surface of a carbon support. Generally, tellurium deposition onto the catalyst precursor may be achieved by many techniques known in the art. Such methods include liquid phase methods such as reaction deposition techniques (e.g., deposition via reduction of metal compounds and deposition via hydrolysis of metal compounds), ion exchange techniques, excess solution impregnation and incipient wetness impregnation; vapor phase methods such as physical deposition and chemical deposition; precipitation; electrochemical deposition; and electroless deposition. See generally, Ebner et al., U.S. Pat. No. 6,417,133, Leiber et al., U.S. Pat. No. 6,586,621 and Cameron et al., "Carbons as Supports for Precious Metal Catalysts," *Catalysis Today*, 7, 113–137 (1990).

1. Oxidative Deposition of Tellurium

In accordance with the present invention, it has been discovered that conventional metal deposition techniques may not provide optimum results when depositing tellurium, particularly with respect to metal dispersion and adhesion. Experience to date suggests that conventional techniques used to deposit tellurium onto a catalyst precursor comprising a noble metal such as platinum at the surface of a carbon support achieve varying and sometimes unsatisfactory results with respect to the dispersion of tellurium at the surface of the precursor and retention of tellurium as the catalyst is subsequently used to catalyze liquid phase oxidation reactions. Thus, the present invention provides an improved method for delivering and depositing tellurium onto the surface of a noble metal on carbon catalyst precursor so as to provide a substantially uniform dispersion of tellurium stably fixed to the catalyst surface.

In contrast to some conventional methods used to deposit metals in catalyst preparation, it has been surprisingly discovered that tellurium is advantageously deposited onto a catalyst precursor under oxidative conditions. In particular, it has been discovered that oxidative conditions are better at stably "fixing" tellurium at the surface of the catalyst precursor than reductive deposition techniques which attempt to deposit tellurium in its elemental state. Depositing tellurium at the surface of a catalyst precursor under oxidative conditions provides a tellurium-promoted, noble metal on carbon catalyst that does not lose a significant amount of tellurium upon use in liquid phase oxidation reactions. Without being bound to a particular theory, it is believed that tellurium-promoted catalysts prepared under oxidative conditions exhibit less tellurium leaching because tellurium is deposited onto the surface of the catalyst precursor in the form of one or more tellurium species which are better able to fix or adhere to the catalyst surface than elemental tellurium. It is believed that tellurium may be deposited in a variety of forms under oxidative conditions that are generally less soluble in liquid phase oxidation reaction media. For example, tellurium deposited onto the precursor under oxidative conditions may be present at the surface of the catalyst in the form of ionized tellurium or oxygenated or oxidized tellurium such as tellurium dioxide ($TeO_2$) or mixtures of such species. Furthermore, it is believed that depositing tellurium under oxidative conditions in accordance with the present invention is effective to uniformly disperse deposited tellurium species on the noble metal at the surface of the catalyst precursor. Oxidative deposition may preferentially deposit tellurium onto the noble metal and other metals present at the surface of the catalyst precursor such that at least about 40%, preferably at least about 50%, more preferably at least about 75%, still more preferably at least about 90%, even more preferably at least about 95% and especially substantially all of the deposited tellurium atoms are associated with or bound to metals at the surface of the catalyst precursor as opposed to being deposited on the carbon support.

In one embodiment, the process for oxidative deposition of tellurium generally comprises combining an oxidation catalyst precursor and a source of tellurium in a liquid medium to form an oxidation catalyst precursor slurry. An oxygen-containing gas is introduced into the catalyst precursor slurry such that tellurium is transported to and deposited on a surface of the catalyst precursor under oxidative conditions to form a tellurium-promoted oxidation catalyst.

The oxidation catalyst precursor may take a variety of forms and preferably comprises a noble metal at the surface of a carbon support in a proportion selected so as to provide an oxidation catalyst of the desired composition. If the catalyst is to include one or more promoter metals in addition to tellurium, it is preferred that the tellurium be deposited over a catalyst precursor comprising appropriate quantities of the noble metal and promoter metal(s) at the surface of a carbon support. For example, the catalyst precursor may comprise a noble metal alloyed with one or more non-tellurium promoter metals to form alloyed metal particles. As used herein, the term "alloy" encompasses any metal particle comprising a noble metal and at least one promoter metal, irrespective of the precise manner in which the noble metal and promoter metal atoms are disposed within the particle. The alloyed metal particles need not have a uniform composition and the compositions may vary from particle to particle, or even within the particles themselves, although it is generally preferable to have a portion of the noble metal atoms at the surface of the alloyed metal particle. The catalyst precursor may comprise particles at the surface of the carbon support comprising noble and promoter metal alloys of various types, including intermetallic compounds, substitutional alloys, multiphasic alloys, segregated alloys and interstitial alloys. However, rather than an alloy, the catalyst precursor may comprise particles consisting of the noble metal alone and/or the non-tellurium promoter metal(s) alone at the surface of the carbon support. Nevertheless, it is preferred, although not essential, that the majority of noble metal atoms at the surface of the catalyst precursor be alloyed with any non-tellurium promoter metal present, and more preferred that substantially all of the noble metal atoms be alloyed with the promoter metal(s) employed. If the promoter metal is a noble metal as well, the non-promoter noble metal is likewise preferably alloyed with the promoter metal noble metal. As an example, the catalyst precursor over which tellurium is deposited may suitably comprise a pre-formed, "deeply reduced" noble metal or noble metal/promoter metal alloy on carbon catalyst as described by Ebner et al., U.S. Pat. No. 6,417,133 and Leiber et al., U.S. Pat. No. 6,586,621, the entire disclosures of which are incorporated herein by reference. However, there are a variety of alternative preparative techniques known in the art which may be used to form a multi-metallic, carbon supported catalyst precursor and the present invention is not limited in this respect. See, for example, V. Ponec & G. C. Bond, *Catalysis by Metals and Alloys*, "Studies in Surface Science and Catalysis," Vol. 95 (B. Delmon. & J. T. Yates, advisory eds., Elsevier Science B. V., Amsterdam, Netherlands).

Alternatively, the catalyst precursor may comprise a used noble metal on carbon oxidation catalyst (i.e., an oxidation catalyst that has been used previously in catalyzing one or more oxidation reactions). For example, the activity and/or desired selectivity of a catalyst typically decreases with use over several reaction cycles. In particular, in the context of the liquid phase oxidation of N-(phosphonomethyl) iminodiacetic acid substrates, the activity of a carbon-supported, noble metal-containing catalyst with respect to oxidation of formaldehyde and formic acid by-products often tends to slowly decrease as the catalyst is used, thereby causing less formic acid and/or formaldehyde to be destroyed and, consequently, a greater amount of NMG to be produced. Eventually, this activity will decrease to an unacceptable level and the catalyst mass must be replaced. However, in accordance with the present invention, such a used or spent catalyst may be reinvigorated (i.e., the activity and/or selectivity of the catalyst for oxidizing an N-(phosphonomethyl)iminodiacetic acid substrate to produce an N-(phosphonomethyl)glycine product can be increased to an acceptable level) by depositing tellurium onto the surface of the used catalyst precursor. In other words, tellurium can be deposited onto the surface of a used catalyst to modify and improve catalyst performance and extend the useful life of the catalyst.

A variety of tellurium sources may be combined with the catalyst precursor in the catalyst precursor slurry. For example, suitable tellurium sources generally include any inorganic or organic tellurium compounds containing tellurium atoms at an oxidation level greater than 0 (e.g., 2, 3, 4, 5 or 6), most preferably 4. Examples of suitable tellurium compounds include tellurium oxides (e.g., $TeO_2$, $Te_2O_3$, $Te_2O_5$, $TeO_3$ and the like); tellurium salts of inorganic hydracids including, for example, tellurium tetrachloride ($TeCl_4$), tellurium tetrabromide ($TeBr_4$), tellurium tetraiodide ($TeI_4$) and the like; tellurium salts of inorganic oxyacids including, for example, tellurious acid ($H_2TeO_3$), telluric acid ($H_2TeO_4$ or $Te(OH)_6$), tellurium nitrate ($Te_2O_4.HNO_3$) and the like; and miscellaneous other organic and inorganic tellurium compounds including, for example, dimethyl tellurium dichloride, lead tellurium oxide, tellurium isopropoxide, ammonium tellurate, tellurium thiourea and the like. Preferably, the source of tellurium comprises a tellurium oxide or tellurium salt of an inorganic hydracid. More preferably, the tellurium compound is tellurium dioxide ($TeO_2$), tellurium tetrachloride ($TeCl_4$), or telluric acid ($Te(OH)_6$), with tellurium dioxide being most preferred.

In general, the liquid medium for the catalyst precursor slurry may comprise any suitable liquid selected to be compatible with the tellurium source and the catalyst precursor. Suitable liquids for use in preparing the catalyst precursor slurry include, for example, water and aqueous solutions of formaldehyde and/or formic acid. The catalyst precursor slurry is preferably formed using water as the liquid medium in which the catalyst precursor particles are suspended.

Chelating agents capable of forming coordination compounds with tellurium in the catalyst precursor slurry are disadvantageous in that they tend to sequester tellurium and inhibit transport of tellurium to the surface of the catalyst precursor during oxidative deposition. Accordingly, it is preferred that the catalyst precursor slurry be maintained substantially free of such chelants. That is, the concentration of any chelating agent capable of forming coordination compounds with tellurium in the precursor slurry is sufficiently low so as to not inhibit substantially quantitative delivery of tellurium to the surface of the catalyst precursor. Most preferably, the catalyst precursor slurry is devoid of any chelant capable of binding tellurium so as to better facilitate delivery of tellurium to the surface of the catalyst precursor.

The oxygen-containing gas introduced into the catalyst precursor slurry may be any gaseous mixture comprising molecular oxygen which optionally may comprise one or more diluents. Examples of such gases are air, pure molecular oxygen, or molecular oxygen diluted with helium, argon, nitrogen, or other non-oxidizing gases. For economic reasons, the oxygen source is most preferably air or pure molecular oxygen. The oxygen-containing gas may be introduced into the catalyst precursor slurry by any suitable means, typically by introducing the gas into a vessel containing the slurry. Preferably, the oxygen-containing gas is introduced into the slurry in a manner which facilitates intimate contact between the gas and catalyst precursor particles suspended in the liquid medium. Accordingly, oxygen-containing gas from a pressurized source may be introduced through a small orifice nozzle, sparger conduit, dip tube or similar device submerged in the catalyst precursor slurry near the bottom of the vessel. Dispersion of the oxygen-containing gas throughout the catalyst precursor slurry may be enhanced by agitating the slurry (e.g., with an impeller) so that the turbulence intimately mixes and distributes the oxygen-containing gas as it rises upward through the slurry. Alternatively or additionally, dispersion of the oxygen-containing gas in the catalyst precursor slurry may be enhanced by introducing the gas into the slurry through a diffuser such as a porous frit or by other means well-known to those skilled in the art for promoting gas-liquid phase contact.

The rate at which the oxygen-containing gas is introduced into the liquid medium can vary significantly. However, in order to ensure sufficiently oxidative conditions are maintained and to accomplish substantially quantitative tellurium deposition in a reasonable amount of time, the oxygen-containing gas is suitably introduced into the slurry at a rate of at least about 20 L/min/kg catalyst precursor, preferably from about 20 to about 250 L/min/kg catalyst precursor, more preferably from about 30 to about 175 L/min/kg catalyst precursor and especially from about 40 to about 160 L/min/kg catalyst precursor. Preferably, the dissolved oxygen concentration in the catalyst precursor slurry during oxidative deposition of tellurium is maintained near the saturation concentration. As a reference, the saturation concentration of oxygen in water under standard conditions (25° C. and one atmosphere) is about 8 ppm. It should be understood that in an alternative embodiment, introduction of an oxygen-containing gas into the catalyst precursor slurry can be avoided by adding the catalyst precursor and tellurium source to an oxygenated liquid medium having a dissolved oxygen concentration near the saturation concentration (e.g., a liquid medium previously sparged with an oxygen-containing gas).

The oxidative deposition process for depositing tellurium onto the catalyst precursor may be conducted at any pressure including atmospheric, sub-atmospheric and super-atmospheric pressures. Oxidative deposition of tellurium is suitably carried out at a pressure at or near atmospheric pressure, although moderately pressurizing the catalyst precursor slurry using the oxygen-containing gas may enhance catalyst performance. However, it is believed that pressures much in excess of about 90 psig would unnecessarily complicate the deposition process. Accordingly, if super-atmospheric pressures are employed, it is preferred that the catalyst precursor slurry be maintained at a pressure of no greater than about 90 psig, more preferably at a pressure no greater than about 50 psig, and most preferably at a pressure no greater than about 30 psig.

It is important to note that the temperature of the catalyst precursor slurry appears to significantly effect tellurium deposition under oxidative conditions and later catalyst performance. More particularly, experience to date suggests that tellurium is more stably deposited at the surface of the catalyst precursor under oxidative conditions at a temperature no greater than about 50° C. Accordingly, the temperature of the catalyst precursor slurry during introduction of the oxygen-containing gas is preferably no greater than about 50° C., more preferably no greater than about 40° C., and most preferably no greater than about 30° C. Without being bound to a particular theory, it is believed that lower catalyst precursor slurry temperatures slow the kinetics of tellurium deposition sufficiently to aid in fixing the tellurium to the precursor surface.

Once the tellurium source is added to the catalyst precursor slurry, oxidative deposition is allowed to continue for a time sufficient to achieve substantially quantitative deposition of tellurium on the surface of the catalyst precursor. Under the conditions disclosed herein, satisfactory results are typically obtained after about 30 minutes. At the end of the deposition cycle, the tellurium-promoted catalyst is separated from the slurry (e.g., by filtration). Although the formed catalyst may be subjected to drying (e.g., under vacuum at 80° C. with nitrogen sweep), drying is not necessary and the wet catalyst may be used immediately to catalyze the liquid phase oxidation reaction of interest.

In some applications, the oxidative deposition of tellurium can advantageously be performed using the reactor vessel and appurtenant apparatus employed in carrying out the liquid phase oxidation reaction. That is, a fresh tellurium-promoted, noble metal on carbon catalyst or a used catalyst reinvigorated by tellurium deposition may be prepared at the facility in which it is later put to use. For example, wherein a tellurium-promoted, noble metal on carbon catalyst is used in the liquid phase oxidation of an N-(phosphonomethyl)iminodiacetic acid substrate using an oxygen-containing gas as the oxidizing agent, the tellurium may be deposited onto the catalyst precursor within the reactor vessel prior to the introduction of the N-(phosphonomethyl)iminodiacetic acid substrate. Such on-site catalyst preparation or regeneration provides a significant operational and cost advantage to traditional preparation methods which have required separate processing and/or equipment requirements. However, it is important to recognize that N-(phosphonomethyl)iminodiacetic acid substrates and the resulting N-(phosphonomethyl)glycine product act as tellurium chelating agents. As noted above, such chelating agents tend to undermine the transport of tellurium to the catalyst precursor surface. Accordingly, in such applications, care should be taken to avoid substantial contamination of the catalyst precursor slurry with either the N-(phosphonomethyl)iminodiacetic acid substrate or the N-(phosphonomethyl)glycine product during oxidative deposition of tellurium.

2. Use of an $Fe_2O_3$ Deposition Agent

In accordance with the present invention, processes for preparing tellurium-promoted, noble metal on carbon catalysts may include depositing tellurium onto the surface of a noble metal on carbon oxidation catalyst precursor in the presence of an iron oxide, particularly ferric oxide ($Fe_2O_3$), deposition or dispersion enhancing agent. In such an embodiment, the process comprises contacting an oxidation catalyst precursor and a source of tellurium as previously described along with $Fe_2O_3$ in a liquid medium to deposit tellurium on a surface of the catalyst precursor. Without being bound to a particular theory, it is believed that $Fe_2O_3$ may act as an oxidizing agent that facilitates deposition and stably fixing tellurium species at the surface of the catalyst precursor that are generally less soluble in liquid phase oxidation reaction media such as ionized tellurium or oxygenated or oxidized tellurium such as tellurium dioxide ($TeO_2$). Ferric oxide may also play a role in the slurry reaching the optimum electrochemical potential for tellurium deposition.

The use of $Fe_2O_3$ as a tellurium deposition aid may be utilized in conjunction with many liquid phase deposition techniques including reaction deposition techniques (e.g., deposition via reduction of metal compounds and deposition via hydrolysis of metal compounds), ion exchange techniques, excess solution impregnation, incipient wetness impregnation and electrochemical deposition techniques. For example, $Fe_2O_3$ may facilitate deposition of tellurium using conventional reductive deposition techniques in which the catalyst precursor and tellurium source are contacted in a liquid reducing medium comprising a suitable reducing agent such as an aqueous solution of formaldehyde, formic acid or a mixture thereof. Alternatively, $Fe_2O_3$ may be included as a component of the catalyst precursor slurry prepared in the oxidative deposition of tellurium as described above. The amount of $Fe_2O_3$ combined with the catalyst precursor and tellurium source in the liquid medium is not narrowly critical. For example, suitable results are obtained if the quantity of $Fe_2O_3$ is sufficient to provide at least a substantially equimolar or slight excess of iron relative to tellurium introduced into the liquid medium. The other parameters of the liquid phase deposition technique when $Fe_2O_3$ is utilized as a tellurium deposition aid follow conventional practice well-known to those skilled in the art.

3. Sequential Deposition Followed by Heat Treatment

Another embodiment for preparing the tellurium-promoted, noble metal on carbon catalyst of the present invention comprises the sequential deposition of a noble metal and tellurium onto a carbon support followed by heat treating the formed catalyst. As with oxidative deposition, tellurium is preferably deposited onto a carbon support as described above having a noble metal and one or more non-tellurium promoter metals (e.g., a noble metal/promoter metal alloy) deposited thereon.

In general, the sequential deposition of the noble metal, tellurium and any non-tellurium promoter metal(s) may be accomplished by any means generally known in the art for depositing metals onto a carbon support as described, for example, by Ebner et al., U.S. Pat. No. 6,417,133, by Leiber et al., U.S. Pat. No. 6,586,621, or by Cameron et al. in "Carbons as Supports for Precious Metal Catalysts," *Catalysis Today*, 7, 113–137 (1990). As such, it is typically preferred that the noble metal and any promoter metal(s) be deposited onto the carbon support to form an oxidation catalyst precursor prior to deposition of tellurim. More particularly, the oxidation catalyst precursor may comprise any carbon-supported, noble metal precursor generally described above including, for example, a pre-formed, "deeply reduced" noble metal or noble metal/promoter metal alloy on carbon catalyst as described by Ebner et al., U.S. Pat. No. 6,417,133 and Leiber et al., U.S. Pat. No. 6,586,621 or a used noble metal on carbon catalyst.

In a certain preferred embodiment, tellurium is preferably deposited onto a promoted catalyst precursor. In particular, the catalyst precursor is preferably a carbon support, which may or may not have a noble metal and/or a promoter deposited at its surface, and which has not been subjected to high temperature treatment. Thus, the tellurium is deposited onto the surface of the catalyst precursor prior to high temperature treatment. In a particularly preferred embodiment, tellurium is deposited onto a catalyst precursor comprising a noble metal, preferably platinum, and a promoter, preferably iron, at a surface of a carbon support. Tellurium is preferably deposited onto the surface of the catalyst using a solution comprising a salt of tellurium in one of its more reduced oxidation states as described above. For example, a suitable salt that may be used to deposit tellurium is $TeCl_4$. After tellurium deposition, the catalyst precursor is then subjected to high temperature treatment to form a tellurium-promoted, noble metal on carbon oxidation catalyst. For example, after the carbon support has been impregnated with the noble metal(s), any other metal promoter(s) and tellurium, the catalyst may be subjected to a reductive heat treatment by heating the surface at a temperature of at least about 400° C. It is especially preferable to conduct this heating in a non-oxidizing environment (e.g., nitrogen, argon, or helium). It is also more preferred for the temperature to be greater than about 500° C. Still more preferably, the temperature is from about 550° to about 1,200° C., and most preferably from about 550° to about 900° C. Further details regarding such a reductive, post-deposition heat treatment are disclosed by Ebner et al., U.S. Pat. No. 6,417,133, the entire disclosure of which is incorporated herein by reference.

C. Use of the Oxidation Catalyst

The above-described tellurium-promoted, noble metal on carbon catalyst may be used to catalyze various liquid phase oxidation reactions. Examples of such reactions include the oxidation of alcohols and polyols to form aldehydes, ketones and acids (e.g., the oxidation of 2-propanol to form acetone and the oxidation of glycerol to form glyceraldehyde, dihydroxyacetone, or glyceric acid); the oxidation of aldehydes to form acids (e.g., the oxidation of formaldehyde to form formic acid and the oxidation of furfural to form 2-furan carboxylic acid); the oxidation of tertiary amines to form secondary amines (e.g., the oxidation of nitrilotriacetic acid (NTA) to form iminodiacetic acid ("IDA")); the oxidation of secondary amines to form primary amines (e.g., the oxidation of IDA to form glycine); and the oxidation of various acids (e.g., formic acid or acetic acid) to form carbon dioxide and water.

The above-described catalyst is especially useful in liquid phase oxidation reactions conducted at pH levels less than 7 and in particular, at pH levels less than 3. It also is especially useful in the presence of solvents, reactants, intermediates, or products which tend solubilize noble metals. An example of such a reaction system is the preparation of an N-(phosphonomethyl)glycine product (i.e., N-(phosphonomethyl)glycine or a salt thereof) by catalytic oxidation of an N-(phosphonomethyl)iminodiacetic acid substrate, including the oxidation of the resulting formaldehyde and formic acid by-products in an aqueous reaction mixture. Further, the catalyst of the present invention also has application in oxidizing formaldehyde and formic acid present in aqueous waste streams generated upon purification of the N-(phosphonomethyl)glycine product as disclosed, for example, by Smith, U.S. Pat. No. 5,606,107 and by Leiber et al., U.S. Pat. No. 6,586,621, the entire disclosures of which are incorporated herein by reference. Although the description below will disclose with particularity the use of the above-described tellurium-promoted, noble metal on carbon catalyst to effect the oxidative cleavage of a carboxymethyl substituent from an N-(phosphonomethyl)iminodiacetic acid substrate and oxidation of the resulting formaldehyde and formic acid by-products, it should be recognized, that the principles are generally applicable to other liquid phase oxidative reactions, especially those conducted at pH levels less than 7 and those involving solvents, reactants, intermediates, or products which tend to solubilize noble metals.

As noted above, the use of heterogenous, noble metal on carbon catalysts in the liquid phase oxidation of N-(phosphonomethyl)iminodiacetic acid substrates is well known. Such catalysts are useful in catalyzing the concurrent reactions of (1) the oxidation of the N-(phosphonomethyl)iminodiacetic acid substrate to produce N-(phosphonomethyl)glycine; (2) the oxidation of formaldehyde by-product to produce formic acid; and (3) the further oxidation of formic acid to carbon dioxide and water. The carbon component of the oxidation catalyst provides the primary adsorption site for the oxidation of the N-(phosphonomethyl)iminodiacetic acid substrate to form the N-(phosphonomethyl)glycine product and formaldehyde, while the noble metal component provides the primary adsorption site for the oxidation of formaldehyde and formic acid to ultimately form carbon dioxide and water.

In accordance with the present invention, it has been discovered that tellurium, particularly in the modest amounts deposited onto a noble metal on carbon catalyst as described above, can advantageously effect reaction systems for the liquid phase oxidation of N-(phosphonomethyl)iminodiacetic acid substrates by balancing or matching the reaction rate of the primary reaction (i.e., reaction (1) above) with the reaction rates for the oxidation of the resulting by-products, formaldehyde and formic acid (i.e., reactions (2) and (3) above). Without being bound to a particular theory, it is believed that tellurium, especially modest amounts of tellurium, may slightly slow the oxidative cleavage of the N-(phosphonomethyl)iminodiacetic acid substrate as compared to conventional noble metal on carbon oxidation catalysts. At the same time, the tellurium-promoted catalyst does not substantially effect, or at least diminishes to a much lesser extent, the oxidation rate of the undesired formaldehyde and formic acid by-products produced. In this manner, the catalyst of the present invention tends to equilibrate the rates of these concurrent reactions as conducted under the conditions described herein such that the formaldehyde and formic acid by-products are more effectively removed from the reaction medium as they are generated. As a result, less formaldehyde and formic acid are available in solution to participate in undesirable side reactions that decrease overall N-(phosphonomethyl)glycine product yield and compromise product purity.

The amount of tellurium used in the oxidation catalyst of the present invention is important in controlling the rates of reaction as described above. For example, experience to date suggests catalysts having higher amounts of tellurium (i.e., tellurium in an amount of more than about 0.25% by weight of the catalyst), may overly diminish the oxidation reaction rate of the N-(phosphonomethyl)iminodiacetic acid substrate. Thus, in such applications, it is preferred that tellurium constitutes from about 0.02% to about 0.175% by weight of the oxidation catalyst, more preferably from about 0.02% to about 0.125% by weight of the catalyst, even more preferably from about 0.02% to about 0.1% by weight of the catalyst, still more preferably from about 0.02% to about 0.08% by weight of the catalyst, and especially from about 0.04% to about 0.08% by weight of the catalyst. For example, it is believed that a platinum on carbon oxidation catalyst promoted with about 0.75% by weight tellurium is effective in balancing the rates of these simultaneous oxidation reactions.

As is recognized in the art, the liquid phase oxidation of N-(phosphonomethyl)iminodiacetic acid substrates may be carried out in a batch, semi-batch or continuous reactor system containing one or more oxidation reaction zones. The oxidation reaction zone(s) may be suitably provided by various reactor configurations, including those that have back-mixed characteristics, in the liquid phase and optionally in the gas phase as well, and those that have plug flow characteristics. Suitable reactor configurations having back-mixed characteristics include, for example, stirred tank reactors, ejector nozzle loop reactors (also known as venturi-loop reactors) and fluidized bed reactors. Suitable reactor configurations having plug flow characteristics include those having a packed or fixed catalyst bed (e.g., trickle bed reactors and packed bubble column reactors) and bubble slurry column reactors. Fluidized bed reactors may also be operated in a manner exhibiting plug flow characteristics. The configuration of the reactor system and the number of oxidation reaction zones is not critical to the practice of the present invention. However, it is preferred that the oxidation reactor system employed be adapted for use of a particulate catalyst suspended in the aqueous reaction mixture and include a filter to separate at least a portion of the N-(phosphonomethyl)glycine product from the reaction product mixture comprising the N-(phosphonomethyl)glycine product and the particulate catalyst such that the resulting catalyst slurry fraction comprising the particulate catalyst can be recycled and reintroduced into the oxidation reaction zone(s).

Likewise, conditions, including temperature and pressure maintained in the oxidation reaction zone(s), reagent concentration, catalyst loading or concentration, reaction time, etc., suitable for liquid phase oxidative cleavage of a carboxymethyl substituent from an N-(phosphonomethyl)iminodiacetic acid substrate in an aqueous reaction mixture using an oxidizing agent such as an oxygen-containing gas in the presence of a noble metal on carbon catalyst are well known to those skilled in the art and the selection of these variables is not affected by the practice of the present invention.

Oxidation of the N-(phosphonomethyl)iminodiacetic acid substrate may be conducted at a wide range of temperatures and at pressures ranging from sub-atmospheric to super-atmospheric. Operating at higher temperatures and super-atmospheric pressures, while increasing plant costs, is preferred since such conditions tend to improve phase transfer between the liquid and gas phase and increase the oxidation reaction rate. Moreover, the temperature within the oxidation reaction zone is preferably maintained sufficiently high with respect to the N-(phosphonomethyl)glycine product concentration such that essentially all the N-(phosphonomethyl)glycine product in the reaction product mixture is dissolved. The temperature of the aqueous reaction mixture contacted with the oxygen-containing gas is suitably from about 80° to about 180° C., preferably from about 90° to about 150° C., and more preferably from about 95° to about 110° C. The pressure maintained within the oxidation reaction zone(s) generally depends on the temperature of the aqueous reaction mixture. Preferably, the pressure is sufficient to prevent the reaction mixture from boiling and is adequate to cause the oxygen from the oxygen-containing gas to dissolve into the reaction mixture at a rate sufficient such that oxidation of the N-(phosphonomethyl)iminodiacetic acid substrate is not limited due to an inadequate oxygen supply. Suitable pressures range from about 30 to about 500 psig, and preferably from about 30 to about 130 psig. The concentration of the particulate, tellurium-promoted, noble metal on carbon catalyst and the N-(phosphonomethyl)iminodiacetic acid substrate in the aqueous reaction mixture are not critical. Typically, the catalyst concentration is from about 0.1 to about 10% by weight ([mass of catalyst÷total reaction mass]×100%). Preferably, the catalyst concentration is from about 0.2 to about 5%, and more preferably from about 1 to about 4% by weight. Concentrations greater than about 10% are difficult to separate from the N-(phosphonomethyl) glycine product. On the other hand, concentrations less than about 0.1% tend to produce unacceptably low reaction rates. The concentration of N-(phosphonomethyl)iminodiacetic acid substrate is preferably selected such that all reactants and the N-(phosphonomethyl)glycine product remain in solution so that the suspended particulate catalyst can be recovered for re-use, for example, by filtration. Normally, the concentration of N-(phosphonomethyl)iminodiacetic acid substrate is up to about 25% by weight ([mass of N-(phosphonomethyl)iminodiacetic acid substrate÷total reaction mass]×100%), and with respect to the preferred temperatures of the aqueous reaction mixture, preferably from about 7 to about 15% by weight. The pH of the aqueous reaction mixture is typically less than about 7 and often in the range of from about 1 to about 2. When conducted in a continuous reactor system, the residence time in the oxidation reaction zone can vary widely depending on the specific catalyst employed, catalyst concentration and other conditions. Typically, the residence time can vary over the range of from about 3 to about 120 minutes. Preferably, the residence time is from about 5 to about 90 minutes, and more preferably from about 5 to about 60 minutes. When conducted in a batch reactor system, the reaction time typically varies over the range of from about 15 to about 120 minutes. Preferably, the reaction time is from about 20 to about 90 minutes, and more preferably from about 30 to about 60 minutes.

The oxygen-containing gas used for oxidation of the N-(phosphonomethyl)iminodiacetic acid substrate is any gaseous mixture comprising molecular oxygen which optionally may comprise one or more diluents which are non-reactive with the oxygen or with the substrate or oxidation product under the reaction conditions. Examples of such gases are air, pure molecular oxygen, or molecular oxygen diluted with helium, argon, nitrogen, or other non-oxidizing gases. For economic reasons, the oxygen source is usually air or pure molecular oxygen. Preferably, the oxygen-containing gas comprises at least about 95 mole % $O_2$, typically approximately 98 mole % $O_2$. The oxygen may be contacted with the aqueous reaction mixture by any conventional means in a manner which maintains the dissolved oxygen concentration in the reaction mixture at the desired level and preferably in a manner which maximizes the contact of the gas with the reaction solution. Such contact may be obtained, for example, by dispersing the gas through a diffuser such as a porous frit or sparger immersed in the reaction mixture. The oxygen feed rate preferably is such that oxidation of the N-(phosphonomethyl) iminodiacetic acid substrate is not limited by oxygen supply, but not too high so as to lead to detrimental oxidation of the surface of the noble metal on carbon catalyst.

Suitable reactor systems and oxidation reaction conditions for liquid phase catalytic oxidation of an N-(phosphonomethyl)iminodiacetic acid substrate are described, for example, by Ebner et al., U.S. Pat. No. 6,417,133, by Leiber et al., U.S. Pat. No. 6,586,621, and by Haupfear et al., WO 01/92272, the entire disclosures of which are incorporated herein by reference.

It should be recognized that the tellurium-promoted, noble metal on carbon oxidation catalyst in accordance with this invention may also be combined with other conventional heterogenous catalysts (e.g., a catalyst not containing tellurium) to form a catalyst mass useful in liquid phase oxidation reactions. For example, a tellurium-promoted catalyst may be used to reinvigorate a used catalyst mass and extend the useful life thereof. It should be further recognized that the catalyst of the present invention has the ability to be reused over several cycles (i.e., it may be used to catalyze multiple batches of substrate), depending on how oxidized its surface becomes with use. Even after the catalyst becomes heavily oxidized, it may be reused by being reactivated. To reactivate a catalyst having a heavily oxidized surface, the surface may be first washed to remove the organics from the surface. It may then be reduced in the same manner that a catalyst is reduced after metal deposition as described above.

D. EXAMPLES

The following examples are simply intended to further illustrate and explain the present invention. The invention, therefore, should not be limited to any of the details in these examples.

All analyses for metal content in the following examples were conducted using Inductively Coupled Argon Plasma—Mass Spectroscopy (ICAP-MS).

Example 1

Preparation of a Pt/Fe/Te Catalyst Under Oxidative Conditions

This example demonstrates the preparation of a Pt/Fe/Te catalyst by depositing tellurium onto a platinum-iron catalyst precursor with formic acid under oxidative conditions. To prepare the catalyst, a catalyst precursor comprising 5.0% by weight platinum and 0.48% by weight iron on a particulate carbon support (2.5 g) was added to a one liter stainless steel reactor (Autoclave Engineers) equipped with a sub-surface gas inlet. The catalyst precursor was slurried in a solution of 0.5% formic acid (497.5 g) and $TeO_2$ (0.0026 g) was added. Oxygen was sparged into the reactor at ambient temperature and atmospheric pressure while the catalyst precursor slurry was agitated at a rate of 500 rpm. The rate of oxygen flow into the catalyst precursor slurry was 392 $cm^3$/minute. After 30 minutes, the flow of oxygen was stopped and the catalyst was filtered. The filtered catalyst comprised 5.0% by weight platinum, 0.48% by weight iron and 0.083% by weight tellurium.

Example 2

Preparation of a Pt/Fe/Te Catalyst Under Oxidative Conditions

This example demonstrates the preparation of a Pt/Fe/Te catalyst by depositing tellurium onto a platinum-iron catalyst precursor with formic acid under oxidative conditions. To prepare the catalyst, a catalyst precursor comprising 5.0% by weight platinum and 0.48% by weight iron on a particulate carbon support (2.5 g) was added to a one liter stainless steel reactor (Autoclave Engineers) equipped with a sub-surface gas inlet. The catalyst precursor was slurried in an aqueous solution containing 0.5% formic acid (497.5 g) and $TeO_2$ (0.0016 g) was added. Oxygen was sparged into the reactor at ambient temperature and atmospheric pressure while the catalyst precursor slurry was agitated at a rate of 500 rpm. The rate of oxygen flow into the catalyst precursor slurry was 392 $cm^3$/minute. After 30 minutes, the flow of oxygen was stopped and the catalyst was filtered. The filtered catalyst comprised 5.0% by weight platinum, 0.48% by weight iron and 0.05% by weight tellurium.

Example 3

Preparation of a Pt/Fe/Te Catalyst Under Oxidative Conditions

This example demonstrates the preparation of a Pt/Fe/Te catalyst by depositing tellurium onto a platinum-iron catalyst precursor with formaldehyde under oxidative conditions. To prepare the catalyst, a catalyst precursor comprising 5.0% by weight platinum and 0.48% by weight iron on a particulate carbon support (2.5 g) was added to a one liter stainless steel reactor (Autoclave Engineers) equipped with a sub-surface gas inlet. The catalyst precursor was slurried in an aqueous solution containing 2.5% formaldehyde (497.5 g) and $TeO_2$ (0.0016 g) was added. Oxygen was sparged into the reactor at ambient temperature and atmospheric pressure while the catalyst precursor slurry was agitated at a rate of 500 rpm. The rate of oxygen flow into the catalyst precursor slurry was 392 cm³/minute. After 30 minutes, the flow of oxygen was stopped and the catalyst was filtered. The filtered catalyst comprised 5.0% by weight platinum, 0.48% by weight iron and 0.05% by weight tellurium.

Example 4

Oxidative Deposition of Tellurium Using Various Deposition Solutions

This example compares the use of deionized water, formic acid and formaldehyde as deposition solutions for use in depositing tellurium onto a platinum-iron catalyst precursor under oxidative conditions. To prepare the catalyst, a catalyst precursor comprising 5.0% by weight platinum and 0.48% by weight iron on a particulate carbon support (2.5 g) was added to a one liter stainless steel reactor (Autoclave Engineers) equipped with a sub-surface gas inlet. The catalyst precursor was slurried in the deposition solution (497.5 g) and $TeO_2$ (0.0023 g) was added. Oxygen was sparged into the reactor at ambient temperature and atmospheric pressure while the catalyst precursor slurry was agitated at a rate of 500 rpm. The rate of oxygen flow into the catalyst precursor slurry was 392 cm³/minute. After 30 minutes, the flow of oxygen was stopped and the catalyst was filtered. Each of the prepared catalysts comprised 5.0% by weight platinum, 0.48% by weight iron and 0.075% by weight tellurium on a particulate carbon support. The filtrate was analyzed for the presence of metals. Results of the analysis are shown in Table 1.

TABLE 1

Deposition Results for Example 4.

| Deposition Solution | Filtrate Analysis Results | | |
|---|---|---|---|
| | Pt (ppm) | Fe (ppm) | Te (ppm) |
| 0.5% formic acid | <0.2 | <0.01 | <0.02 |
| 2.5% formic acid | <0.2 | <0.01 | <0.02 |
| 2.5% formaldehyde | <0.2 | 2.6 | <0.02 |
| Deionized Water | <0.2 | 5.6 | <0.02 |

No tellurium was detected in the filtrate from any of the samples indicating that the tellurium remained with the catalyst.

Example 5

Oxidative Deposition of Tellurium at Various Temperatures

This example compares Pt/Fe/Te catalysts prepared by depositing tellurium onto a platinum-iron catalyst precursor under oxidative conditions at ambient temperature (20° C.), at a temperature of 30° C., at a temperature of 50° C. and at a temperature of 80° C. To prepare the catalysts, a catalyst precursor comprising 5.0% by weight platinum and 0.48% by weight iron on a particulate carbon support (2.5 g) was added to a one liter stainless steel reactor (Autoclave Engineers) equipped with a sub-surface gas inlet. The catalyst precursor was slurried in deionized water (497.5 g) and $TeO_2$ (0.0023 g) was added. The catalyst precursor slurry was brought to temperature at atmospheric pressure while under nitrogen. When the slurry reached the target temperature, oxygen was sparged into the reactor at an oxygen flow rate of 392 cm³/minute while the catalyst precursor slurry was agitated at a rate of 500 rpm. After 30 minutes, the flow of oxygen was stopped and the catalyst was filtered. Each of the prepared catalysts comprised 5.0% by weight platinum, 0.48% by weight iron and 0.075% by weight tellurium. The filtrate was analyzed for the presence of metals. Results of the analysis are shown in Table 2.

TABLE 2

Deposition Results for Example 5.

| Deposition Temperature | Filtrate Analysis Results | | |
|---|---|---|---|
| | Pt (ppm) | Fe (ppm) | Te (ppm) |
| Ambient (20° C.) | <0.01 | <0.2 | <0.02 |
| 30° C. | <0.01 | <0.2 | <0.02 |
| 50° C. | 0.01 | <0.2 | 0.41 |
| 80° C. | <0.01 | <0.2 | 0.21 |

Example 6

Use of a Pt/Fe/Te Catalyst for the Oxidation of N-(phosphonomethyl)iminodiacetic Acid This example demonstrates the use of tellurium in the oxidation of N-(phosphonomethyl)iminodiacetic acid to prepare N-(phosphonomethyl)glycine. The example comprised a comparison of four independent experiments for the oxidation of N-(phosphonomethyl)iminodiacetic acid in the presence of a Pt/Fe on carbon catalyst versus Pt/Fe/Te on carbon catalysts prepared in accordance with Example 4 above. The first experiment was conducted using a catalyst comprising 5.0% by weight platinum and 0.48% by weight iron on a particulate carbon support. The second experiment was conducted using a catalyst comprising 5.0% by weight platinum, 0.48% by weight iron and 0.083% by weight tellurium on a particulate carbon support prepared with deionized water as described in Example 4. The third experiment was conducted using a catalyst comprising 5.0% by weight platinum, 0.48% by weight iron and 0.075% by weight tellurium on a particulate carbon support prepared with 0.5% formic acid solution as described in Example 4. The fourth experiment was conducted using a catalyst comprising 5.0% by weight platinum, 0.48% by weight iron and 0.075% by weight tellurium on a particulate carbon support prepared with 2.5% formaldehyde solution as described in Example 4.

The oxidation reactions were conducted in a 1 liter stainless steel reactor (Autoclave Engineers) fitted with an agitator having an impeller located near the bottom of the autoclave. A subsurface sintered metal frit situated below the impeller was provided for introducing oxygen into the reactor. The reactor had an internal catalyst filter for separating the catalyst from the N-(phosphonomethyl)glycine product fraction withdrawn from the reactor at the conclusion of the oxidation reaction.

Each reaction series included twelve (12) N-(phosphonomethyl)iminodiacetic acid batch oxidation reactions reusing the same catalyst charge. For the first oxidation reaction in each series, the catalyst (2.5 g) and N-(phosphonomethyl)iminodiacetic acid (60.5 g) were charged to the reactor with make-up solution to 500 g total reaction mass (0.5% catalyst loading). The make-up solution contained 0.1% formaldehyde and 0.5% formic acid. Fresh catalyst was used at the start of each reaction series. The impeller speed was set at 1000 rpm. At zero time, 392 cm$^3$/minute of oxygen was introduced into the agitated aqueous reaction mixture at 100° C. and 110 psig. After about 28 minutes, the oxygen flow was dropped to 125 cm$^3$/minute and held at that rate for about 5 minutes past the point where the N-(phosphonomethyl)iminodiacetic acid was depleted. The catalyst was then separated from the reaction product mixture containing N-(phosphonomethyl) glycine to form an isolated catalyst slurry fraction and a product fraction. The isolated catalyst was then used in the next oxidation reaction in the series. This process was repeated for each reaction such that the initial catalyst charge was recovered and reused for each of the subsequent 11 oxidation batch reactions in the series.

The reaction product fraction from each reaction was analyzed by high pressure liquid chromatography (HPLC) to determine the composition with respect to the following: N-(phosphonomethyl)glycine (glyphosate), formaldehyde (CH$_2$O), formic acid (HCO$_2$H), N-(phosphonomethyl) iminodiacetic acid (PMIDA), aminomethylphosphonic acid+N-methylaminomethylphosphonic acid (AMPA+ MAMPA), N-methyl-N-(phosphonomethyl)glycine (NMG) and iminodiacetic acid (IDA). The results are reported in Tables 3 to 6 below. Concentrations are in percent by weight. ND indicates "Not Detected." DBNQ indicates "Detected But Not Quantified."

TABLE 3

Oxidation w/5.0% Pt/0.48% Fe on carbon catalyst

| Run | Time (min) | Glyphosate (%) | PMIDA (%) | CH$_2$O (%) | HCO$_2$H (%) | AMPA/MAMPA (%) | NMG (%) | IDA (%) |
|---|---|---|---|---|---|---|---|---|
| 1 | 31.8 | 8.182 | ND | 0.096 | 0.419 | 0.050 | 0.027 | 0.136 |
| 2 | 32 | 8.210 | ND | 0.088 | 0.457 | 0.043 | 0.031 | 0.087 |
| 3 | 31.6 | 8.204 | ND | 0.085 | 0.461 | 0.042 | 0.030 | 0.085 |
| 4 | 31.4 | 8.143 | ND | 0.088 | 0.477 | 0.041 | 0.031 | 0.091 |
| 5 | 31.4 | 8.221 | ND | 0.107 | 0.543 | 0.046 | 0.042 | 0.048 |
| 6 | 31.6 | 8.201 | ND | 0.099 | 0.515 | 0.048 | 0.038 | 0.064 |
| 7 | 31.6 | 8.224 | ND | 0.097 | 0.522 | 0.045 | 0.039 | 0.064 |
| 8 | 31.2 | 8.127 | ND | 0.101 | 0.510 | 0.046 | 0.036 | 0.072 |
| 9 | 31.8 | 8.238 | ND | 0.105 | 0.557 | 0.047 | 0.045 | 0.054 |
| 10 | 30.7 | 8.207 | ND | 0.119 | 0.538 | 0.048 | 0.041 | 0.033 |
| 11 | 31.7 | 8.188 | ND | 0.112 | 0.549 | 0.046 | 0.044 | 0.057 |
| 12 | 31.8 | 8.204 | DBNQ | 0.127 | 0.567 | 0.045 | 0.059 | 0.051 |

*(mass ÷ total reaction mass) × 100%

TABLE 4

Oxidation w/5.0% Pt/0.48% Fe/0.083% Te on carbon catalyst (deionized water)

| Run | Time (min) | Glyphosate (%) | PMIDA (%) | CH$_2$O (%) | HCO$_2$H (%) | AMPA/MAMPA (%) | NMG (%) | IDA (%) |
|---|---|---|---|---|---|---|---|---|
| 1 | 33.9 | 8.046 | 0.012 | 0.031 | 0.281 | 0.035 | 0.018 | 0.125 |
| 2 | 36.1 | 8.484 | 0.009 | 0.017 | 0.262 | 0.026 | 0.016 | 0.058 |
| 3 | 41 | 8.274 | 0.007 | 0.014 | 0.242 | 0.031 | 0.016 | 0.045 |
| 4 | 41.9 | 8.261 | 0.009 | 0.023 | 0.333 | 0.029 | 0.025 | 0.033 |
| 5 | 42.2 | 8.096 | 0.008 | 0.017 | 0.300 | 0.031 | 0.023 | 0.038 |
| 6 | 39.2 | 8.292 | 0.017 | 0.025 | 0.371 | 0.026 | 0.025 | 0.044 |
| 7 | 39.9 | 8.222 | 0.009 | 0.029 | 0.437 | 0.030 | 0.033 | 0.029 |
| 8 | 41.6 | 8.303 | 0.007 | 0.035 | 0.396 | 0.031 | 0.030 | 0.030 |
| 9 | 40.6 | 8.089 | 0.013 | 0.037 | 0.455 | 0.032 | 0.039 | 0.024 |
| 10 | 42.3 | 8.017 | 0.012 | 0.041 | 0.431 | 0.028 | 0.034 | 0.034 |
| 11 | 43.7 | 8.212 | 0.008 | 0.049 | 0.443 | 0.034 | 0.042 | 0.028 |
| 12 | 43.6 | 8.214 | 0.008 | 0.045 | 0.417 | 0.032 | 0.035 | 0.032 |

*(mass ÷ total reaction mass) × 100%

TABLE 5

Oxidation w/5.0% Pt/0.48% Fe/0.075% Te on carbon (0.5% formic acid) catalyst

| Run | Time (min) | Glyphosate (%) | PMIDA (%) | CH$_2$O (%) | HCO$_2$H (%) | AMPA/MAMPA (%) | NMG (%) | IDA (%) |
|---|---|---|---|---|---|---|---|---|
| 1 | 33.2 | 7.936 | ND | 0.055 | 0.347 | 0.032 | 0.027 | 0.109 |
| 2 | 34.0 | 8.110 | 0.005 | 0.061 | 0.402 | 0.026 | 0.035 | 0.059 |
| 3 | 33.7 | 8.111 | ND | 0.057 | 0.441 | 0.028 | 0.033 | 0.058 |
| 4 | 33.7 | 8.012 | 0.006 | 0.056 | 0.510 | 0.026 | 0.041 | 0.069 |
| 5 | 33.7 | 8.059 | 0.006 | 0.065 | 0.540 | 0.026 | 0.042 | 0.060 |
| 6 | 34.1 | 8.051 | 0.009 | 0.062 | 0.588 | 0.029 | 0.050 | 0.034 |
| 7 | 34.5 | 8.054 | 0.047 | 0.079 | 0.601 | 0.026 | 0.054 | 0.032 |
| 8 | 33.9 | 8.038 | 0.005 | 0.069 | 0.570 | 0.029 | 0.045 | 0.045 |

TABLE 5-continued

Oxidation w/5.0% Pt/0.48% Fe/0.075% Te on carbon (0.5% formic acid) catalyst

| Run | Time (min) | Glyphosate (%) | PMIDA (%) | CH$_2$O (%) | HCO$_2$H (%) | AMPA/MAMPA (%) | NMG (%) | IDA (%) |
|---|---|---|---|---|---|---|---|---|
| 9  | 34.6 | 8.047 | 0.010 | 0.075 | 0.603 | .031  | 0.055 | 0.032 |
| 10 | 34.8 | 8.108 | 0.013 | 0.083 | 0.606 | 0.031 | 0.057 | 0.029 |
| 11 | 33.7 | 8.003 | 0.004 | 0.081 | 0.599 | 0.032 | 0.051 | 0.033 |
| 12 | 34.7 | 8.043 | 0.013 | 0.089 | 0.648 | 0.032 | 0.062 | 0.029 |

*(mass ÷ total reaction mass) × 100%

TABLE 6

Oxidation w/5.0% Pt/0.48% Fe/0.075% Te on carbon (2.5% formaldehyde) catalyst

| Run | Time (min) | Glyphosate (%) | PMIDA (%) | CH$_2$O (%) | HCO$_2$H (%) | AMPA/MAMPA (%) | NMG (%) | IDA (%) |
|---|---|---|---|---|---|---|---|---|
| 1  | 33.6 | 8.022 | ND    | 0.049 | 0.281 | 0.034 | 0.018 | 0.148 |
| 2  | 34.4 | 8.187 | 0.005 | 0.061 | 0.376 | 0.029 | 0.032 | 0.054 |
| 3  | 36   | 8.255 | 0.016 | 0.065 | 0.394 | 0.024 | 0.038 | 0.040 |
| 4  | 35.7 | 8.179 | 0.016 | 0.060 | 0.418 | 0.021 | 0.033 | 0.052 |
| 5  | 34.9 | 8.170 | 0.017 | 0.064 | 0.477 | 0.025 | 0.035 | 0.050 |
| 6  | 35.8 | 8.167 | 0.024 | 0.067 | 0.504 | 0.028 | 0.043 | 0.034 |
| 7  | 36.1 | 8.207 | 0.027 | 0.072 | 0.525 | 0.024 | 0.047 | 0.031 |
| 8  | 34.2 | 8.078 | 0.016 | 0.072 | 0.547 | 0.026 | 0.041 | 0.044 |
| 9  | 35.7 | 8.012 | 0.037 | 0.078 | 0.577 | 0.025 | 0.052 | 0.029 |
| 10 | 34.8 | 8.100 | 0.010 | 0.078 | 0.569 | 0.031 | 0.046 | 0.035 |
| 11 | 36.6 | 7.917 | 0.014 | 0.077 | 0.595 | 0.028 | 0.058 | 0.023 |
| 12 | 33.2 | 8.578 | 0.003 | 0.074 | 0.525 | 0.037 | 0.044 | 0.034 |

*(mass ÷ total reaction mass) × 100%

Example 7

Preparation and Use of a Pt/Fe/Te Catalyst for N-(phosphonomethyl)iminodiacetic Acid Oxidation This example demonstrates the preparation of a tellurium-promoted oxidation catalyst and its use in the oxidation of N-(phosphonomethyl)iminodiacetic acid to N-(phosphonomethyl)glycine as compared to a platinum-iron oxidation catalyst without tellurium.

To prepare the tellurium-promoted catalyst, a catalyst precursor comprising 5.0% by weight platinum and 0.48% by weight iron on a particulate carbon support (2.5 g) was added to a 300 mL stainless steel reactor (Autoclave Engineers) fitted with an agitator and gas introduction through a subsurface sintered metal frit (below the agitator impeller). The catalyst precursor was slurried in a solution of deionized water (176.4 g) and TeO$_2$ (0.0034 g) was added. Oxygen was sparged into the reactor at ambient temperature and atmospheric pressure while the catalyst precursor slurry was agitated at a rate of 500 rpm. The rate of oxygen flow into the catalyst precursor slurry was 141 cm$^3$/minute. After 30 minutes, the flow of oxygen was stopped and the catalyst was filtered. The catalyst remaining in the autoclave comprised 5.0% by weight platinum, 0.48% by weight iron and 0.075% by weight tellurium.

The oxidation experiments comprised oxidizing N-(phosphonomethyl)iminodiacetic acid in a series of 30 individual batch reactions wherein the catalyst was re-used. For the first oxidation reaction in each series, the catalyst (3.6 g) and N-(phosphonomethyl)iminodiacetic acid (21.8 g) were charged to the reactor with make-up solution to 180 g total reaction mass (2.0% catalyst loading). The make-up solution contained 0.1% formaldehyde and 0.5% formic acid. Fresh catalyst was used at the start of each reaction series. The reactor was heated under nitrogen atmosphere to the operating temperature of 100° C. and the oxygen introduction began when the temperature had risen to about 97° C. The temperature was controlled at 100° C. throughout the course of the reaction. The agitator stirring rate was 900 rpm. The operating pressure was 90 psig oxygen during the reactions. Oxygen was first introduced at the rate of 141 cm$^3$/minute for 28 minutes and then the flow was step-ramped down to 45 cm$^3$/minute for the remainder of the reaction. When the reaction was finished (oxidation of N-(phosphonomethyl)iminodiacetic acid is essentially completed) the product was removed at the operating temperature by forcing it under pressure through a subsurface sintered metal frit, up the tubing and out of the autoclave through a valve and into a flask. The product was then neutralized with ammonium hydroxide to keep the product from precipitating out of solution. The isolated catalyst was then used in the next oxidation reaction in the series. This process was repeated for each reaction such that the initial catalyst charge was recovered and reused for each of the subsequent 29 oxidation batch reactions in the series.

The reaction product fraction from each reaction was analyzed by high pressure liquid chromatography (HPLC) to determine the composition with respect to the following: N-(phosphonomethyl)glycine (glyphosate), formaldehyde (CH$_2$O), formic acid (HCO$_2$H), N-(phosphonomethyl) iminodiacetic acid (PMIDA), aminomethylphosphonic acid+N-methylaminomethylphosphonic acid (AMPA+MAMPA), N-methyl-N-(phosphonomethyl)glycine (NMG) and iminodiacetic acid (IDA). The levels of reaction product impurities were compared to a benchmark 30-run reaction series using the platinum-iron catalyst precursor without tellurium. Results are shown in Tables 7 and 8. Concentrations are in percent by weight. ND indicates "Not Detected." DBNQ indicates "Detected But Not Quantified."

TABLE 7

30-run oxidation results for Pt/Fe/Te on carbon catalyst of Example 7.

| Run | Time (min) | Glyphosate (%) | PMIDA (%) | CH$_2$O (%) | HCO$_2$H (%) | AMPA/MAMPA (%) | NMG (%) | IDA (%) |
|---|---|---|---|---|---|---|---|---|
| 1 | 42.2 | 7.740 | 0.011 | 0.0007 | 0.003 | 0.079 | ND | 0.285 |
| 2 | 39.7 | 8.160 | 0.009 | 0.0006 | 0.004 | 0.081 | ND | 0.137 |
| 3 | 40.9 | 8.250 | 0.008 | 0.0006 | 0.004 | 0.060 | ND | 0.116 |
| 4 | 41.5 | 8.560 | 0.008 | 0.0014 | 0.012 | 0.047 | ND | 0.101 |
| 5 | 43.6 | 8.050 | 0.014 | 0.0004 | 0.012 | 0.169 | ND | 0.098 |
| 6 | 37.6 | 8.440 | 0.005 | 0.0006 | 0.011 | 0.042 | ND | 0.066 |
| 7 | 40 | 8.390 | 0.004 | 0.0003 | 0.008 | 0.047 | ND | 0.083 |
| 8 | 45.4 | 8.760 | 0.015 | 0.0006 | 0.007 | 0.110 | ND | 0.084 |
| 9 | 38.4 | 8.410 | 0.005 | 0.0004 | 0.005 | 0.071 | ND | 0.077 |
| 10 | 39.2 | 8.350 | 0.007 | 0.0005 | 0.006 | 0.107 | ND | 0.079 |
| 11 | 39.3 | 8.550 | 0.011 | 0.0003 | 0.007 | 0.061 | ND | 0.081 |
| 12 | 39.5 | 8.560 | 0.008 | 0.0006 | 0.005 | 0.083 | ND | 0.086 |
| 13 | 40.4 | 8.460 | 0.009 | 0.0003 | 0.006 | 0.047 | ND | 0.081 |
| 14 | 39.6 | 8.720 | 0.006 | 0.0003 | 0.007 | 0.032 | ND | 0.085 |
| 15 | 38.4 | 8.520 | 0.007 | 0.0005 | 0.009 | 0.045 | ND | 0.069 |
| 16 | 40.9 | 8.460 | 0.014 | 0.0008 | 0.024 | 0.023 | ND | 0.081 |
| 17 | 39.5 | 8.563 | 0.022 | 0.0012 | 0.021 | 0.023 | ND | 0.086 |
| 18 | 39.2 | 8.651 | 0.021 | 0.0010 | 0.025 | 0.024 | ND | 0.089 |
| 19 | 38.7 | 8.457 | 0.067 | 0.0011 | 0.050 | 0.038 | ND | 0.075 |
| 20 | 40.2 | 8.634 | 0.015 | 0.0014 | 0.019 | 0.024 | ND | 0.090 |
| 21 | 40.0 | 8.429 | 0.015 | 0.0006 | 0.019 | 0.025 | ND | 0.089 |
| 22 | 39.8 | 8.476 | 0.022 | 0.0007 | 0.024 | 0.022 | ND | 0.096 |
| 23 | 39.6 | 8.443 | 0.024 | 0.0006 | 0.030 | 0.023 | ND | 0.091 |
| 24 | 39.8 | 8.330 | 0.032 | 0.0008 | 0.030 | 0.023 | ND | 0.093 |
| 25 | 40.3 | 8.555 | 0.009 | 0.0006 | 0.011 | 0.028 | ND | 0.090 |
| 26 | 41.4 | 8.388 | 0.021 | 0.0008 | 0.027 | 0.027 | ND | 0.086 |
| 27 | 40.6 | 8.473 | 0.045 | 0.0014 | 0.037 | 0.025 | ND | 0.097 |
| 28 | 40.9 | 8.500 | 0.025 | 0.0008 | 0.031 | 0.026 | ND | 0.096 |
| 29 | 39.7 | 8.609 | 0.032 | 0.0010 | 0.034 | 0.025 | ND | 0.092 |
| 30 | 40.1 | 8.420 | 0.018 | 0.0008 | 0.023 | 0.026 | ND | 0.093 |

* (mass ÷ total reaction mass) × 100%

TABLE 8

30-run oxidation results for Pt/Fe on carbon catalyst of Example 7.

| Run | Time (min) | Glyphosate (%) | PMIDA (%) | CH$_2$O (%) | HCO$_2$H (%) | AMPA/MAMPA (%) | NMG (%) | IDA (%) |
|---|---|---|---|---|---|---|---|---|
| 1 | 35.6 | 7.782 | 0.218 | 0.023 | 0.160 | 0.055 | 0.012 | 0.232 |
| 2 | 39.9 | 8.306 | 0.076 | 0.006 | 0.107 | 0.036 | 0.005 | 0.118 |
| 3 | 40.3 | 8.425 | 0.018 | 0.0012 | 0.067 | 0.037 | ND | 0.113 |
| 4 | 41.6 | 8.427 | 0.016 | 0.0011 | 0.065 | 0.035 | ND | 0.114 |
| 5 | 41.2 | 8.270 | 0.033 | 0.0012 | 0.093 | 0.032 | ND | 0.114 |
| 6 | 41.3 | 8.242 | 0.010 | 0.0008 | 0.048 | 0.035 | ND | 0.120 |
| 7 | 42.2 | 8.393 | 0.030 | 0.0012 | 0.088 | 0.032 | ND | 0.117 |
| 8 | 35.6 | 7.972 | 0.451 | 0.0066 | 0.192 | 0.026 | ND | 0.121 |
| 9 | 41.4 | 8.407 | 0.031 | 0.0012 | 0.093 | 0.031 | ND | 0.128 |
| 10 | 39.4 | 8.366 | 0.024 | 0.0008 | 0.081 | 0.029 | ND | 0.120 |
| 11 | 40.1 | 8.341 | 0.056 | 0.0015 | 0.108 | 0.027 | 0.002 | 0.120 |
| 12 | 39.4 | 8.351 | 0.034 | 0.0010 | 0.088 | 0.028 | ND | 0.121 |
| 13 | 39.6 | 8.263 | 0.083 | 0.0028 | 0.123 | 0.026 | 0.002 | 0.122 |
| 14 | 39.7 | 8.256 | 0.066 | 0.0025 | 0.118 | 0.030 | 0.003 | 0.124 |
| 15 | 39.1 | 8.333 | 0.027 | 0.0057 | 0.091 | 0.028 | ND | 0.120 |
| 16 | 39.6 | 8.339 | 0.056 | 0.0024 | 0.114 | 0.027 | 0.002 | 0.118 |
| 17 | 39.5 | 8.307 | 0.039 | 0.0020 | 0.107 | 0.028 | 0.002 | 0.118 |
| 18 | 39.7 | 8.292 | 0.066 | 0.0026 | 0.118 | 0.037 | 0.007 | 0.125 |
| 19 | 38.9 | 8.262 | 0.059 | 0.0025 | 0.119 | 0.027 | 0.002 | 0.117 |
| 20 | 39.8 | 8.353 | 0.018 | 0.0012 | 0.075 | 0.029 | 0.002 | 0.119 |
| 21 | 39.8 | 8.299 | 0.054 | 0.0026 | 0.114 | 0.027 | 0.003 | 0.116 |
| 22 | 39.8 | 8.234 | 0.074 | 0.0033 | 0.121 | 0.025 | ND | 0.119 |
| 23 | 40.1 | 8.371 | 0.052 | 0.0026 | 0.116 | 0.026 | ND | 0.117 |
| 24 | 40.4 | 8.396 | 0.060 | 0.0037 | 0.116 | 0.025 | 0.002 | 0.127 |
| 25 | 39.3 | 8.298 | 0.028 | 0.0022 | 0.090 | 0.026 | ND | 0.115 |
| 26 | 39.4 | 8.295 | 0.088 | 0.0049 | 0.156 | 0.044 | 0.007 | 0.092 |
| 27 | 40.3 | 8.308 | 0.044 | 0.0035 | 0.125 | 0.025 | 0.006 | 0.110 |
| 28 | 39.7 | 8.317 | 0.063 | 0.0046 | 0.135 | 0.025 | 0.006 | 0.111 |
| 29 | 39.3 | 8.323 | 0.073 | 0.0048 | 0.139 | 0.024 | 0.005 | 0.110 |
| 30 | 39.4 | 8.378 | 0.038 | 0.0029 | 0.109 | 0.025 | 0.005 | 0.111 |

* (mass ÷ total reaction mass) × 100%

Example 8

Preparation of a Pt/Fe/Te Catalyst Using $Fe_2O_3$

This example demonstrates the use of $Fe_2O_3$ in depositing tellurium onto a platinum-iron catalyst precursor to prepare a Pt/Fe/Te catalyst. To prepare the catalyst, a catalyst precursor comprising a 5.0% by weight platinum and 1.0% by weight iron on a particulate carbon support (6.0 g) and an aqueous solution of 0.5% formic acid (400 mL) was placed in a 3-necked round-bottom flask fitted with a thermometer and a condenser. The catalyst precursor slurry was stirred by magnetic stirrer at ambient temperature and atmospheric pressure. $TeO_2$ (0.0075 g), $Fe_2O_3$ (0.005 g) and $10^{-3}$ M formic acid (400 mL) were added. The $TeO_2$ and $Fe_2O_3$ were separately washed into the catalyst precursor slurry with a portion of the $10^{-3}$ M formic acid before the remaining formic acid was added. The mixture was stirred overnight and vacuum filtered under nitrogen to recover the catalyst. The catalyst was rinsed with $10^{-3}$ M formic acid solution (150 mL), recovered and dried at 80° C. under vacuum with a nitrogen sweep. The recovered catalyst comprised 5.0% by weight platinum, 1.0% by weight iron and 0.1% by weight tellurium.

Example 9

Preparation of a Pt/Fe/Te Catalyst Using $Fe_2O_3$

This example demonstrates the use of $Fe_2O_3$ in depositing tellurium onto a platinum-iron catalyst precursor to prepare a Pt/Fe/Te catalyst. To prepare the catalyst, a catalyst precursor comprising a 5.0% by weight platinum and 1.0% by weight iron on a particulate carbon support (6.0 g) was slurried with an aqueous solution of 0.5% formic acid (400 mL) in a 3-necked round-bottom flask fitted with a thermometer and a condenser. The catalyst precursor slurry was stirred by magnetic stirrer at ambient temperature and atmospheric pressure. $TeO_2$ (0.00375 g), $Fe_2O_3$ (0.005 g) and $10^{-3}$ M formic acid (400 mL) were added. The $TeO_2$ and $Fe_2O_3$ were separately washed into the catalyst precursor slurry with a portion of the $10^{-3}$ M formic acid before the remaining formic acid was added. The mixture was stirred overnight and vacuum filtered under nitrogen to recover the catalyst. The catalyst was rinsed with $10^{-3}$ M formic acid solution (150 mL), recovered and dried at 80° C. under vacuum with a nitrogen sweep. The recovered catalyst comprised 5.0% by weight platinum, 1.0% by weight iron and 0.05% by weight tellurium.

Example 10

Use of a Pt/Fe/Te Catalyst for the Oxidation of N-(phosphonomethyl)iminodiacetic Acid This example demonstrates the use of tellurium as a surface promoter for the oxidation of N-(phosphonomethyl) iminodiacetic acid. The example compares independent experiments for the oxidation of N-(phosphonomethyl) iminodiacetic acid in the presence of catalysts comprising platinum and iron versus catalysts comprising platinum, iron and tellurium as prepared in Examples 8 and 9 above. The first experiment was conducted using a catalyst comprising 5.0% by weight platinum and 1.0% by weight iron on a particulate carbon support. The second experiment was conducted using the catalyst of Example 8 comprising 5.0% by weight platinum, 1.0% by weight iron and 0.1% by weight tellurium on a particulate carbon support. The third experiment was conducted using the catalyst of Example 9 comprising 5.0% by weight platinum, 1.0% by weight iron and 0.05% by weight tellurium on a particulate carbon support.

Each experiment comprised oxidizing N-(phosphonomethyl)iminodiacetic acid in a series of six (6) individual batch reactions wherein the catalyst was re-used. For the first oxidation reaction in each series, the catalyst (0.9 g) and N-(phosphonomethyl)iminodiacetic acid (21.8 g) were charged to the reactor with make-up solution to 180 g total reaction mass (0.5% catalyst loading). The make-up solution contained 0.1% formaldehyde and 0.5% formic acid. Fresh catalyst was used at the start of each reaction series. The reactor was heated under nitrogen atmosphere and oxygen introduction began when the temperature had risen to about 97° C. The temperature was controlled at 100° C. throughout the course of the reaction. The agitator stirring rate was 900 rpm. The operating pressure was 90 psig. Oxygen was first introduced at the rate of 141 $cm^3$/minute for 28 minutes and then the flow was step-ramped down to 45 $cm^3$/minute for the remainder of the reaction. When the reaction was finished, the product was removed at the operating temperature by forcing it under pressure through a subsurface sintered metal frit, up the tubing and out of the autoclave through a valve and into a flask. The product was then neutralized with ammonium hydroxide to keep the product from precipitating out of solution. The isolated catalyst was then used in the next oxidation reaction in the series. This process was repeated for each reaction such that the initial catalyst charge was recovered and reused for each of the subsequent 5 oxidation batch reactions in the series.

The reaction product fraction from each reaction was analyzed by high pressure liquid chromatography (HPLC) to determine the composition with respect to the following: N-(phosphonomethyl)glycine (glyphosate), formaldehyde ($CH_2O$), formic acid ($HCO_2H$), N-(phosphonomethyl) iminodiacetic acid (PMIDA), aminomethylphosphonic acid+N-methylaminomethylphosphonic acid (AMPA+ MAMPA), N-methyl-N-(phosphonomethyl)glycine (NMG) and iminodiacetic acid (IDA). Results are shown in Tables 9 to 11. Concentrations are in percent by weight. ND indicates "Not Detected." DBNQ indicates "Detected But Not Quantified."

TABLE 9

| | | | Oxidation w/5.0% Pt/1.0% Fe on carbon catalyst | | | | | |
|---|---|---|---|---|---|---|---|---|
| Run | Time (min) | Glyphosate (%) | PMIDA (%) | $CH_2O$ (%) | $HCO_2H$ (%) | AMPA/MAMPA (%) | NMG (%) | IDA (%) |
| 1 | 33.0 | 7.691 | 0.095 | 0.048 | 0.297 | 0.041 | 0.015 | 0.366 |
| 2 | 33.5 | 8.051 | 0.154 | 0.025 | 0.278 | 0.028 | 0.016 | 0.212 |
| 3 | 33.1 | 7.904 | 0.104 | 0.019 | 0.295 | 0.026 | 0.012 | 0.262 |
| 4 | 33.6 | 7.846 | 0.150 | 0.020 | 0.363 | 0.024 | 0.012 | 0.267 |

TABLE 9-continued

Oxidation w/5.0% Pt/1.0% Fe on carbon catalyst

| Run | Time (min) | Glyphosate (%) | PMIDA (%) | CH$_2$O (%) | HCO$_2$H (%) | AMPA/MAMPA (%) | NMG (%) | IDA (%) |
|---|---|---|---|---|---|---|---|---|
| 5 | 33.6 | 7.983 | 0.144 | 0.019 | 0.374 | 0.026 | 0.015 | 0.230 |
| 6 | 33.6 | 8.020 | 0.135 | 0.019 | 0.376 | 0.025 | 0.013 | 0.222 |

*(mass ÷ total reaction mass) × 100%

TABLE 10

Oxidation w/5.0% Pt/1.0% Fe/0.1% Te on carbon catalyst

| Run | Time (min) | Glyphosate (%) | PMIDA (%) | CH$_2$O (%) | HCO$_2$H (%) | AMPA/MAMPA (%) | NMG (%) | IDA (%) |
|---|---|---|---|---|---|---|---|---|
| 1 | 39.7 | 7.985 | 0.006 | 0.008 | 0.137 | 0.059 | ND | 0.338 |
| 2 | 40.9 | 8.297 | 0.004 | 0.004 | 0.133 | 0.049 | ND | 0.160 |
| 3 | 40.8 | 8.190 | 0.005 | 0.002 | 0.145 | 0.040 | ND | 0.142 |
| 4 | 41.2 | 8.400 | 0.002 | 0.001 | 0.144 | 0.036 | 0.009 | 0.105 |
| 5 | 41.7 | 8.330 | 0.009 | 0.015 | 0.198 | 0.030 | 0.014 | 0.097 |
| 6 | 42.0 | 8.335 | 0.013 | 0.009 | 0.174 | 0.034 | 0.013 | 0.085 |

*(mass ÷ total reaction mass) × 100%

TABLE 11

Oxidation w/5.0% Pt/1.0% Fe/0.05% Te on carbon catalyst

| Run | Time (min) | Glyphosate (%) | PMIDA (%) | CH$_2$O (%) | HCO$_2$H (%) | AMPA/MAMPA (%) | NMG (%) | IDA (%) |
|---|---|---|---|---|---|---|---|---|
| 1 | 32.6 | 7.570 | 0.058 | 0.023 | 0.284 | 0.034 | 0.050 | 0.115 |
| 2 | 33.2 | 7.990 | 0.091 | 0.015 | 0.283 | 0.026 | 0.058 | 0.092 |
| 3 | 33.5 | 7.890 | 0.121 | 0.018 | 0.319 | 0.021 | 0.056 | 0.110 |
| 4 | 33.3 | 7.920 | 0.142 | 0.037 | 0.373 | 0.021 | 0.056 | 0.111 |
| 5 | 33.6 | 7.920 | 0.195 | 0.025 | 0.372 | 0.021 | 0.058 | 0.110 |
| 6 | 33.9 | 7.930 | 0.189 | 0.030 | 0.382 | 0.021 | 0.057 | 0.111 |

*(mass ÷ total reaction mass) × 100%

Example 11

Deposition of Tellurium Onto a Used Catalyst

This example describes the preparation and use of a tellurium-promoted oxidation catalyst wherein the catalyst precursor comprises a used catalyst. The catalyst was prepared by depositing tellurium onto a catalyst precursor comprising an oxidation catalyst containing 5.0% by weight platinum and 0.5% by weight iron on a particulate carbon support which had been previously used in 248 commercial batch reactions for the oxidation of N-(phosphonomethyl) iminodiacetic acid.

The experiment comprised oxidizing N-(phosphonomethyl)iminodiacetic acid in a series of sixteen (16) individual batch reactions in a 300 mL stainless steel reactor (Autoclave Engineers) fitted with an agitator and gas introduction through a subsurface sintered metal frit (below the agitator impeller). The first five oxidation reactions were completed with the used catalyst. After the fifth oxidation reaction, tellurium was deposited onto the catalyst as described below for use in the remainder of the oxidation reactions in the series.

For the first oxidation reaction, the used catalyst (0.9 g) and N-(phosphonomethyl)iminodiacetic acid (21.8 g) were charged to the reactor with make-up solution to 180 g total reaction mass (0.5% catalyst loading). The make-up solution contained 0.1% formaldehyde and 0.5% formic acid. The reactor was heated under nitrogen. When the temperature had risen to about 97° C., oxygen was sparged into the reactor. Oxygen was first introduced at the rate of 141 cm$^3$/minute for 28 minutes and then the flow was step-ramped down to 45 cm$^3$/minute for the remainder of the reaction. The temperature was controlled at 100° C. throughout the course of the reaction. The agitator stirring rate was 900 rpm. The operating pressure was 90 psig. When the reaction was finished, the product was removed at the operating temperature by forcing it under pressure through a subsurface sintered metal frit, up the tubing and out of the autoclave through a valve and into a flask. The product was then neutralized with ammonium hydroxide to keep the product from precipitating out of solution. The isolated catalyst was then used in the next oxidation reaction in the series. This process was repeated for each reaction such that the initial catalyst charge was recovered and reused for each of the oxidation batch reactions.

After the fifth oxidation batch reaction, tellurium was deposited onto the used catalyst under oxidative conditions. The used catalyst remaining in the reactor served as the catalyst precursor which was slurried in deionized water (176.4 g). TeO$_2$ (0.0027 g) was added and oxygen was sparged into the reactor at ambient temperature and atmospheric pressure while the catalyst precursor slurry was agitated at a rate of 500 rpm. The rate of oxygen flow into the catalyst precursor slurry was 141 cm$^3$/minute. The rate of oxygen flow into the catalyst precursor slurry was 141 cm$^3$/minute. After 30 minutes, the flow of oxygen was stopped and the catalyst was filtered. The catalyst, which comprised 5.0% platinum, 0.48% iron and 0.06% tellurium, remained in the reactor and was used in conducting subsequent oxidation reactions 6 to 16.

The reaction product fraction from each reaction was analyzed by high pressure liquid chromatography (HPLC) to determine the composition with respect to the following: N-(phosphonomethyl)glycine (glyphosate), formaldehyde (CH$_2$O), formic acid (HCO$_2$H), N-(phosphonomethyl)iminodiacetic acid (PMIDA), aminomethylphosphonic acid+N-methylaminomethylphosphonic acid (AMPA+MAMPA) and N-methyl-N-(phosphonomethyl)glycine (NMG). Results are shown in Tables 9 to 11. Concentrations are in percent by weight. ND indicates "Not Detected." DBNQ indicates "Detected But Not Quantified."

TABLE 12

Oxidation Results for Example 11.

| Run | Time (min) | Glyphosate (%) | PMIDA (%) | CH$_2$O (%) | HCO$_2$H (%) | AMPA/MAMPA (%) | NMG (%) | IDA (%) |
| --- | --- | --- | --- | --- | --- | --- | --- | --- |
| 1 | 33.6 | 8.212 | 0.035 | 0.010 | 0.176 | 0.011 | ND | 0.141 |
| 2 | 40.6 | 8.166 | 0.101 | 0.010 | 0.186 | 0.037 | ND | 0.101 |
| 3 | 42.3 | 8.443 | 0.084 | 0.008 | 0.167 | 0.013 | ND | 0.111 |
| 4 | 44.7 | 8.201 | 0.072 | 0.004 | 0.152 | 0.013 | ND | 0.111 |
| 5 | 38.7 | 8.241 | 0.090 | 0.007 | 0.210 | 0.009 | ND | 0.105 |
| 6 | 35.3 | 8.077 | 0.169 | 0.004 | 0.087 | 0.013 | ND | 0.082 |
| 7 | 42.7 | 8.481 | 0.029 | 0.003 | 0.054 | 0.009 | ND | 0.082 |
| 8 | 41.7 | 8.475 | 0.065 | 0.002 | 0.057 | 0.009 | ND | 0.082 |
| 9 | 40.9 | 8.540 | 0.029 | 0.003 | 0.060 | 0.009 | ND | 0.070 |
| 10 | 37.8 | 8.429 | 0.127 | 0.005 | 0.114 | 0.007 | ND | 0.068 |
| 11 | 40.5 | 8.451 | 0.028 | 0.003 | 0.070 | 0.009 | ND | 0.067 |
| 12 | 40.4 | 8.403 | 0.055 | 0.004 | 0.092 | 0.009 | ND | 0.063 |
| 13 | 41.0 | 8.550 | 0.067 | 0.006 | 0.097 | 0.013 | ND | 0.060 |
| 14 | 41.3 | 8.690 | 0.049 | 0.006 | 0.095 | 0.014 | ND | 0.056 |
| 15 | 39.0 | 8.590 | 0.071 | 0.006 | 0.103 | 0.013 | 0.001 | 0.055 |
| 16 | 41.1 | 8.600 | 0.016 | 0.003 | 0.077 | 0.015 | ND | 0.054 |

*(mass ÷ total reaction mass) × 100%

Example 12

Preparation of a Pt/Fe/Te Catalyst with Subsequent High-Temperature Treatment

This example demonstrates the preparation of a Pt/Fe/Te catalyst through the sequential deposition of tellurium over a platinum-iron catalyst precursor. To prepare the catalyst, a catalyst precursor comprising platinum and iron on a particulate carbon support (2.5 g) was slurried in water (300 g). The catalyst precursor, which had not been subjected to high temperature treatment, comprised 5.0% by weight platinum and 0.5% by weight iron. TeO$_2$ (0.02 g) was then added to the catalyst precursor slurry and the mixture was heated to 100° C. under pressure (60 psig) in a nitrogen atmosphere for 75 minutes. After heating, the slurry was hot filtered to produce a wet cake which was washed with water (150 g). The cake was then dried at 120° C. under vacuum for 8 to 10 hours. Drying produced a catalyst containing 5% by weight platinum, 0.5% by weight iron and 0.2% by weight tellurium on carbon upon heating at 860° C. in hydrogen for 90 minutes.

Example 13

Use of a Pt/Fe/Te Catalyst in Oxidation Reactions

This example demonstrates the use of tellurium as a surface promoter for the oxidation of formic acid and formaldehyde. The example comprised a comparison of independent reactions for the oxidation of formic acid and formaldehyde in the presence of a Pt/Fe on carbon catalyst and a Pt/Fe/Te on carbon catalyst.

The experiments comprised oxidizing formic acid and formaldehyde in six individual batch reactions for each of the catalysts. The first experiment was conducted using a catalyst containing 5.0% by weight platinum and 0.65% by weight iron. The second experiment was conducted using a catalyst containing 5.0% by weight platinum, 0.65% by weight iron and 0.5% by weight tellurium. The second catalyst was prepared by sequential deposition of tellurium followed by high temperature treatment using a procedure such as that described in Example 12.

All reactions were carried out in a 300 ml stainless steel reactor (Autoclave Engineers) using 0.9 g catalyst (0.5% by weight of the total reaction mass), 21.8 g N-(phosphonomethyl)iminodiacetic acid (12.1% by weight of the total reaction mass), 1000 ppm formaldehyde, 5000 ppm formic acid, a total reaction mass of 180 g, a pressure of 90 psig, a temperature of 100° C. and an agitation rate of 900 rpm. The oxygen feed rate for the first 28 minutes was 141 cm$^3$/minute, and then 45 cm$^3$/minute until 5 minutes after the N-(phosphonomethyl)iminodiacetic acid was essentially depleted.

Results are shown in Tables 13 and 14.

TABLE 13

Oxidation of formic acid and formaldehyde using a Pt/Fe on carbon catalyst

| Time (min) | Formic Acid (ppm) | Formaldehyde (ppm) |
| --- | --- | --- |
| 0 | 5409 | 3304 |
| 5 | 4580 | 1742 |
| 10 | 3732 | 1174 |
| 15 | 2941 | 821 |
| 25 | 1896 | 410.9 |
| 35 | 1129 | 174 |

TABLE 14

Oxidation of formic acid and formaldehyde using a Pt/Fe/Te on carbon catalyst

| Time (min) | Formic Acid (ppm) | Formaldehyde (ppm) |
| --- | --- | --- |
| 0 | 5570 | 3460 |
| 5 | 4280 | DBNQ |
| 10 | 3046 | ND |
| 15 | 2187 | 57.54 |

TABLE 14-continued

Oxidation of formic acid and formaldehyde using a Pt/Fe/Te on carbon catalyst

| Time (min) | Formic Acid (ppm) | Formaldehyde (ppm) |
|---|---|---|
| 25 | 850.2 | 36.16 |
| 35 | 218.5 | 9.81 |

DBNQ = detected but not quantified
ND = not detected

Example 14

Use of a Pt/Fe/Te Catalyst for the Oxidation of N-(phosphonomethyl) Iminodiacetic Acid This example demonstrates the use of tellurium as a surface promoter for the oxidation of N-(phosphonomethyl) iminodiacetic acid to prepare N-(phosphonomethyl)glycine. The example comprised a comparison of three independent experiments for the oxidation of N-(phosphonomethyl) iminodiacetic acid in the presence of a Pt/Fe on carbon catalyst, a Pt/Fe/Te on carbon catalyst and a Pt/Fe/Bi on carbon catalyst.

The experiments comprised oxidizing N-(phosphonomethyl)iminodiacetic acid in six individual batch reactions for each of the catalysts. The first experiment was conducted using a catalyst containing 5.0% by weight platinum and 0.65% by weight iron. The second experiment was conducted using a catalyst containing 5.0% by weight platinum, 0.65% by weight iron and 0.5% by weight tellurium. The third experiment was conducted using a catalyst containing 5.0% by weight platinum, 0.65% by weight iron and 0.8% by weight bismuth.

All reactions were carried out in a 300 ml stainless steel reactor (Autoclave Engineers) using 0.9 g catalyst (0.5% by weight of the total reaction mass), 21.8 g N-(phosphonomethyl)iminodiacetic acid (12.1% by weight of the total reaction mass), 1000 ppm formaldehyde, 5000 ppm formic acid, a total reaction mass of 180 g, a pressure of 90 psig, a temperature of 100° C. and an agitation rate of 900 rpm. The oxygen feed rate for the first 28 minutes was 141 $cm^3$/minute and then 45 $cm^3$/minute until 5 minutes after the N-(phosphonomethyl)iminodiacetic acid was essentially depleted.

Results are shown in Tables 15 through 17.

TABLE 15

Oxidation of PMIDA w/ 5.0% Pt/0.65% Fe catalyst

| Exp. No. | Run Time (min) | Glyphosate (%) | PMIDA (%) | CH$_2$O (%) | HCO$_2$H (%) | AMPA/MAMPA (%) | NMG (%) |
|---|---|---|---|---|---|---|---|
| 1 | 34 | 6.939 | 0.430 | 0.108 | 0.508 | 0.029 | 0.042 |
| 2 | 37.1 | 7.629 | 0.301 | 0.075 | 0.517 | 0.026 | 0.045 |
| 3 | 39.9 | 7.602 | 0.325 | 0.080 | 0.558 | 0.029 | 0.057 |
| 4 | 43.3 | 7.666 | 0.288 | 0.084 | 0.578 | 0.029 | 0.063 |
| 5 | 45 | 7.717 | 0.284 | 0.094 | 0.582 | 0.031 | 0.058 |
| 6 | 45.8 | 7.654 | 0.154 | 0.136 | 0.568 | 0.033 | 0.061 |

*(mass ÷ total reaction mass) × 100%

TABLE 16

Oxidation of PMIDA w/ 5.0% Pt/0.65% Fe/0.5 % Te catalyst

| Exp. No. | Run Time (min) | Glyphosate (%) | PMIDA (%) | CH$_2$O (%) | HCO$_2$H (%) | AMPA/MAMPA (%) | NMG (%) |
|---|---|---|---|---|---|---|---|
| 1 | 49.6 | 7.40 | 0.006 | ND | ND | 0.073 | 0.000 |
| 2 | 56.5 | 7.93 | ND | ND | ND | 0.116 | 0.000 |
| 3 | 62.3 | 8.14 | 0.006 | ND | ND | 0.062 | 0.000 |
| 4 | 67 | 8.54 | 0.012 | 0.006 | ND | 0.026 | 0.000 |
| 5 | 69.6 | 8.56 | 0.008 | 0.008 | ND | 0.052 | 0.000 |
| 6 | 67.9 | 8.82 | 0.003 | 0.006 | ND | 0.049 | 0.000 |

*(mass ÷ total reaction mass) × 100%
ND = Not Detected

TABLE 17

Oxidation of PMIDA w/ 5.0% Pt/0.65% Fe/0.8% Bi catalyst

| Exp. No. | Run Time (min) | Glyphosate (%)* | PMIDA (%)* | CH$_2$O (%)* | HCO$_2$H (%)* | AMPA/MAMPA (%)* | NMG (%)* |
|---|---|---|---|---|---|---|---|
| 1 | 46.7 | 7.634 | 0.027 | 0.015 | 0.017 | 0.046 | 0.005 |
| 2 | 46.4 | 8.087 | 0.008 | 0.025 | 0.021 | 0.058 | 0.000 |
| 3 | 49 | 8.376 | 0.032 | 0.025 | ND | 0.052 | 0.005 |
| 4 | 50.4 | 8.400 | 0.026 | 0.016 | ND | 0.040 | 0.008 |
| 5 | 54.7 | 8.463 | 0.034 | 0.033 | 0.018 | 0.035 | 0.009 |
| 6 | 52.9 | 8.322 | 0.009 | 0.016 | ND | 0.051 | 0.006 |

*(mass ÷ total reaction mass) × 100%
ND = "not detected"

Example 15

Effect of Tellurium on Platinum Leaching in Oxidation Reactions

This example demonstrates the reduction of platinum leaching by the use of tellurium as a surface promoter for the oxidation of N-(phosphonomethyl)iminodiacetic acid to prepare N-(phosphonomethyl)glycine. The example comprised a comparison of three independent experiments for the oxidation of N-(phosphonomethyl)iminodiacetic acid in the presence of a Pt/Fe/Te on carbon catalyst.

The experiments comprised oxidizing N-(phosphonomethyl)iminodiacetic acid in six individual batch reactions for each of the catalysts. The first experiment was conducted using a catalyst containing 5.0% by weight platinum, 0.65% by weight iron and 0.1% by weight tellurium. The second experiment was conducted using a catalyst containing 5.0% by weight platinum, 0.65% by weight iron and 0.25% by weight tellurium. The third experiment was conducted using a catalyst containing 5.0% by weight platinum, 0.65% by weight iron and 0.5% by weight tellurium.

All reactions were carried out in a 300 ml stainless steel reactor (Autoclave Engineers) using 0.9 g catalyst (0.5% by weight of the total reaction mass), 21.8 g N-(phosphonomethyl)iminodiacetic acid (12.1% by weight of the total reaction mass), 1000 ppm formaldehyde, 5000 ppm formic acid, a total reaction mass of 180 g, a pressure of 90 psig, a temperature of 100° C. and an agitation rate of 900 rpm. The oxygen feed rate for the first 28 minutes was 141 cm$^3$/minute and then 45 cm$^3$/minute until 5 minutes after the N-(phosphonomethyl)iminodiacetic acid was essentially depleted.

After the reactions were completed, the product solution was separated from the catalyst and neutralized with caustic. Resulting product solutions were analyzed for the first, second and sixth reactions by ICP-MS (inductively coupled plasma—mass spectroscopy). Results correlating Pt loss with Te content are shown in Tables 18 through 20.

TABLE 18

Platinum leaching results for oxidation w/ 5% Pt/0.65% Fe/0.1% Te catalyst

| Cycle | 1 | 2 | 6 |
|---|---|---|---|
| Pt in sol., ppm | 0.23 | 0.14 | 0.2 |
| Fe in sol., ppm | 13.2 | 1.8 | 0.5 |
| Te in sol., ppm | 0.2 | <0.1 | <0.1 |
| % Pt loss | 0.09 | 0.06 | 0.08 |
| % Fe loss | 40.63 | 5.54 | 1.54 |
| % Te loss | 4 | <2 | <2 |

TABLE 19

Platinum leaching results for oxidation w/ 5% Pt/0.65% Fe/0.25% Te catalyst

| Cycle | 1 | 2 | 6 |
|---|---|---|---|
| Pt in sol., ppm | 0.18 | 0.11 | 0.11 |
| Fe in sol., ppm | 12.3 | 1.5 | 0.6 |
| Te in sol., ppm | 1 | <0.1 | <0.1 |
| % Pt loss | 0.07 | 0.04 | 0.04 |
| % Fe loss | 37.86 | 4.62 | 1.85 |
| % Te loss | 8.00 | <0.8 | <0.8 |

TABLE 20

Platinum leaching results for oxidation w/ 5% Pt/0.65% Fe/0.5% Te catalyst

| Cycle | 1 | 2 | 6 |
|---|---|---|---|
| Pt in sol., ppm | 0.16 | 0.11 | 0.16 |
| Fe in sol., ppm | 10.2 | 1.1 | 0.5 |
| Te in sol., ppm | 0.3 | <0.1 | <0.1 |
| % Pt loss | 0.06 | 0.04 | 0.06 |
| % Fe loss | 31.39 | 3.39 | 1.54 |
| % Te loss | 1.2 | <0.4 | <0.4 |

Example 16

Effect of Tellurium on Platinum Leaching

This example further demonstrates the reduction of platinum leaching by the use of tellurium as a surface promoter for the oxidation of N-(phosphonomethyl) iminodiacetic acid to prepare N-(phosphonomethyl)glycine. The example comprised a comparison of two independent experiments for the oxidation of N-(phosphonomethyl) iminodiacetic acid in the presence of a Pt/Fe/Te on carbon catalyst.

The experiments comprised oxidizing N-(phosphonomethyl)iminodiacetic acid in six individual batch reactions for each of the catalysts. The first experiment was conducted using a catalyst containing 5.0% by weight platinum, 0.48% by weight iron and 0.1% by weight tellurium. The second experiment was conducted using a catalyst containing 5.0% by weight platinum, 0.48% by weight iron and 0.25% by weight tellurium.

All reactions were carried out in a 300 ml stainless steel reactor (Autoclave Engineers) using 0.9 g catalyst (0.5% by weight of the total reaction mass), 21.8 g N-(phosphonomethyl)iminodiacetic acid (12.1% by weight of the total reaction mass), 1000 ppm formaldehyde, 5000 ppm formic acid, a total reaction mass of 180 g, a pressure of 90 psig, a temperature of 100° C. and an agitation rate of 900 rpm. The oxygen feed rate for the first 28 minutes was 141 cm$^3$/minute and then 45 cm$^3$/minute until 5 minutes after the N-(phosphonomethyl)iminodiacetic acid was essentially depleted.

After the reactions were completed, the product solution was separated from the catalyst and neutralized with caustic. Resulting product solutions were analyzed for the first, second and sixth reactions by ICP-MS (inductively coupled plasma—mass spectroscopy). Results correlating Pt loss with Te content are shown in Tables 21 and 22.

TABLE 21

Platinum leaching results for oxidation w/ 5% Pt/0.48% Fe/0.1% Te catalyst

| Cycle | 1 | 2 | 6 |
|---|---|---|---|
| Pt in sol., ppm | 0.09 | 0.08 | 0.11 |
| Fe in sol., ppm | 6.90 | <0.3 | <0.3 |
| Te in sol., ppm | 0.10 | <0.1 | <0.1 |
| % Pt loss | 0.04 | 0.03 | 0.04 |
| % Fe loss | 27.60 | <1.2 | <1.2 |
| % Te loss | 2.00 | <2.0 | <2.0 |

TABLE 22

Platinum leaching results for oxidation w/ 5% Pt/0.65% Fe/0.25% Te catalyst

| Cycle | 1 | 2 | 6 |
|---|---|---|---|
| Pt in sol., ppm | 0.05 | 0.05 | 0.06 |
| Fe in sol., ppm | 8.1 | 0.3 | 0.3 |
| Te in sol., ppm | 0.5 | <0.1 | <0.1 |
| % Pt loss | 0.02 | 0.02 | 0.024 |
| % Fe loss | 32.4 | 1.2 | 1.2 |
| % Te loss | 4 | <0.8 | <0.8 |

Example 17

Effect of Tellurium on Formic Acid and Formaldehyde Formation

This example demonstrates the effect of tellurium as a surface promoter in reducing formic acid and formaldehyde generation during the oxidation of N-(phosphonomethyl)iminodiacetic acid to prepare N-(phosphonomethyl)glycine. The example comprised a comparison of two independent experiments for the oxidation of N-(phosphonomethyl)iminodiacetic acid in the presence of a Pt/Fe/Te on carbon catalyst.

The experiments comprised oxidizing N-(phosphonomethyl)iminodiacetic acid in six individual batch reactions for each of the catalysts. Each experiment was conducted using a catalyst containing 5.0% by weight platinum, 0.65% by weight iron and 0.25% by weight tellurium.

All reactions were carried out in a one liter stainless steel reactor (Autoclave Engineers) using 2.5 g catalyst (0.5% by weight of the total reaction mass), 60.5 g N-(phosphonomethyl)iminodiacetic acid (12.1% by weight of the total reaction mass), 1000 ppm formaldehyde, 5000 ppm formic acid, a total reaction mass of 500 g, a pressure of 90 psig, a temperature of 100° C. and an agitation rate of 900 rpm. The first experiment utilized an oxygen feed rate for the first 28 minutes of 392 $cm^3$/minute and then 125 $cm^3$/minute until 5 minutes after the N-(phosphonomethyl)iminodiacetic acid was essentially depleted. The second experiment used an oxygen feed rate of 278 $cm^3$/minute for the entire reaction until 5 minutes after the N-(phosphonomethyl)iminodiacetic acid was essentially depleted.

Results are shown in Tables 23 and 24.

TABLE 23

Oxidation w/ 5.0% Pt/0.65% Fe/0.25% Te catalyst with a flow change after 28 min

| Exp. No. | Run Time (min) | Glyphosate (%) | PMIDA (%)* | $CH_2O$ (%)* | $HCO_2H$ (%)* | AMPA/MAMPA (%)* | NMG (%)* |
|---|---|---|---|---|---|---|---|
| 1 | 53.4 | 7.726 | 0.016 | ND | 0.038 | 0.062 | 0.000 |
| 2 | 51.8 | 8.371 | ND | 0.002 | 0.072 | 0.054 | 0.000 |
| 3 | 53.3 | 8.591 | 0.010 | 0.002 | ND | 0.049 | 0.000 |
| 4 | 62 | 8.661 | 0.013 | 0.002 | 0.066 | 0.039 | 0.000 |
| 5 | 56.9 | 8.630 | 0.011 | 0.002 | ND | 0.042 | 0.000 |
| 6 | 66.8 | 8.686 | ND | 0.001 | ND | 0.046 | 0.000 |
| 7 | 63.7 | 8.520 | ND | 0.001 | ND | 0.041 | 0.000 |

*(mass ÷ total reaction mass) × 100%

TABLE 24

Oxidation w/ 5.0% Pt/0.65% Fe/0.5% Te catalyst and no flow change

| Exp. No. | Run Time (min) | Glyphosate (%)* | PMIDA (%)* | $CH_2O$ (%)* | $HCO_2H$ (%)* | AMPA/MAMPA (%)* | NMG (%)* |
|---|---|---|---|---|---|---|---|
| 1 | 51.4 | 7.535 | 0.042 | ND | ND | 0.081 | 0.000 |
| 2 | 52.7 | 8.123 | 0.035 | ND | ND | 0.069 | 0.000 |
| 3 | 53.8 | 8.227 | 0.039 | ND | 0.017 | 0.069 | 0.000 |
| 4 | 53.7 | 8.287 | 0.012 | ND | ND | 0.069 | 0.000 |
| 5 | 56.2 | 9.281 | 0.031 | ND | 0.024 | 0.065 | 0.000 |
| 6 | 53.4 | 8.215 | 0.038 | ND | 0.025 | 0.068 | 0.000 |
| 7 | 63.8 | 8.470 | 0.041 | ND | 0.023 | 0.061 | 0.000 |

*(mass ÷ total reaction mass) × 100%

Example 18

Use of Tellurium as a Surface Promoter

This example compares the performance of two catalysts containing tellurium as a surface promoter in the oxidation of N-(phosphonomethyl)iminodiacetic acid.

The example comprised oxidizing N-(phosphonomethyl)iminodiacetic acid in six individual batch reactions for each of the two catalysts. The first experiment was conducted using a catalyst containing 5.0% by weight platinum, 0.5% by weight iron and 0.1% by weight tellurium. The second experiment was conducted using a catalyst containing 5.0% by weight platinum, 0.5% by weight iron and 0.125% by weight tellurium. Both catalysts were prepared by sequential deposition of tellurium followed by high temperature treatment using a procedure such as that described in Example 12.

All reactions were carried out in a 300 ml stainless steel reactor (Autoclave Engineers) using 0.9 g catalyst (0.5% by weight of the total reaction mass), 21.8 g N-(phosphonomethyl)iminodiacetic acid (12.1% by weight of the total reaction mass), 1000 ppm formaldehyde, 5000 ppm formic acid, a total reaction mass of 180 g, a pressure of 90 psig, a temperature of 100° C. and an agitation rate of 900 rpm. The oxygen feed rate for the first 28 minutes was 141 cm$^3$/minute and then 45 cm$^3$/minute until the N-(phosphonomethyl)iminodiacetic acid was essentially depleted.

Results are shown in Tables 25 and 26.

continuous oxidation reactor system using a combination of Pt/Fe and Pt/Fe/Te heterogeneous particulate catalysts.

The reactions were conducted in a continuous reactor system utilizing a 2-liter Hastelloy C autoclave (Autoclave Engineers Inc., Pittsburgh, Pa.). The reactor was equipped with an agitator having a 1.25" diameter six-blade turbine impeller, which was operated at 1600 RPM. The liquid level in the reactor was monitored using a Drexelbrook Universal III™ Smart Level™, with a Teflon-coated sensing element. An internal cooling coil was utilized to control the temperature within the reactor during the course of the reaction.

In the first experiment, the reactor was loaded with a Pt/Fe heterogenous particulate catalyst (2.18 g) and an aqueous slurry feed material (1448 g). The catalyst comprised platinum (5% by weight) and iron (0.5% by weight). The aqueous slurry feed material comprised NN-(phosphonomethyl)iminodiacetic acid (3.5% by weight), glyphosate (1.5% by weight), formaldehyde (1200 ppm by weight) and formic acid (2500 ppm by weight). The slurry feed also contained NaCl (580 ppm by weight) to mimic NaCl impurity.

The reactor was pressurized to 100 psi with nitrogen and heated to 100° C. Once at temperature, a continuous flow of gaseous oxygen was fed to the reactor without any liquid flow through the system. After 9 minutes, the continuous slurry feed was initiated at a rate of 70.4 g/minute and a oxygen flow was continued as described in Table 43 below. A liquid product stream containing glyphosate product was continuously withdrawn from the reactor and analyzed by HPLC. Oxidation results are also presented in Table 27.

TABLE 25

Oxidation of PMIDA w/ 5.0% Pt/0.5% Fe/0.1% Te catalyst

| Exp. No. | Run Time (min) | Glyphosate (%) | PMIDA (%) | CH$_2$O (%) | HCO$_2$H (%) | AMPA/MAMPA (%) | NMG (%) |
|---|---|---|---|---|---|---|---|
| 1 | 42.1 | 8.037 | 0.055 | 0.016 | 0.185 | 0.053 | 0.018 |
| 2 | 44.7 | 8.203 | 0.013 | 0.012 | 0.189 | 0.046 | 0.016 |
| 3 | 45.9 | 8.332 | 0.035 | 0.018 | 0.209 | 0.033 | 0.021 |
| 4 | 45.5 | 8.516 | 0.041 | 0.018 | 0.158 | 0.039 | 0.022 |
| 5 | 47.0 | 8.302 | 0.045 | 0.023 | 0.227 | 0.033 | 0.023 |
| 6 | 47.2 | 8.305 | 0.016 | 0.018 | 0.221 | 0.037 | 0.020 |

*(mass ÷ total reaction mass) × 100%

TABLE 26

Oxidation of PMIDA w/ 5.0% Pt/0.5% Fe/0.125% Te catalyst

| Exp. No. | Run Time (min) | Glyphosate (%) | PMIDA (%) | CH$_2$O (%) | HCO$_2$H (%) | AMPA/MAMPA (%) | NMG (%) |
|---|---|---|---|---|---|---|---|
| 1 | 38.3 | 8.030 | 0.014 | 0.043 | 0.437 | 0.042 | 0.031 |
| 2 | 64.9 | 8.270 | 0.014 | 0.041 | ND | 0.065 | 0.005 |
| 3 | 64.3 | 7.920 | 0.017 | 0.030 | ND | 0.067 | ND |
| 4 | 42.7 | 8.130 | 0.021 | 0.465 | 0.057 | 0.084 | 0.055 |
| 5 | 35.3 | 7.790 | 0.008 | 0.504 | 0.052 | 0.072 | 0.039 |
| 6 | 37.4 | 8.160 | 0.011 | 0.553 | 0.073 | 0.097 | 0.073 |
| 7 | 30 | 8.140 | 0.029 | 0.560 | 0.065 | 0.127 | 0.047 |

*(mass ÷ total reaction mass) × 100%

Example 19

Comparison of Pt/Fe Catalyst Versus a Mixture of Pt/Fe and Pt/Fe/Te Catalysts This example compares the conversion of N-(phosphonomethyl)iminodiacetic acid to glyphosate in a continuous oxidation reactor system using a Pt/Fe heterogeneous particulate catalyst versus the conversion of NN-(phosphonomethyl)iminodiacetic acid to glyphosate in a In the second experiment, the reactor was loaded with a Pt/Fe heterogenous particulate catalyst (1.09 g), a Pt/Fe/Te heterogeneous particulate catalyst (1.09 g) and an aqueous slurry feed material (1455 g). The Pt/Fe catalyst comprised platinum (5% by weight) and iron (0.5% by weight) and the Pt/Fe/Te catalyst comprised platinum (5% by weight), iron (0.5% by weight) and tellurium (0.2% by weight). The aqueous slurry feed material comprised NN-(phosphonomethyl)iminodiacetic acid (3.5% by weight), glyphosate (1.5% by weight), formaldehyde (1200 ppm by weight) and formic acid (2500 ppm by weight). The slurry feed also contained NaCl (580 ppm by weight) to mimic NaCl impurity.

The reactor was pressurized to 100 psi with nitrogen and heated to 100° C. Once at temperature, a continuous flow of gaseous oxygen was fed to the reactor without any liquid flow through the system. After 19 minutes, the continuous slurry feed was initiated at a rate of 70.4 g/minute and oxygen flow was continued as described in Table 44 below. A liquid product stream containing glyphosate product was continuously withdrawn from the reactor and analyzed by HPLC. Oxidation results for the second experiment are also presented in Table 28.

The present invention is not limited to the above embodiments and can be variously modified. The above description of preferred embodiments is intended only to acquaint others skilled in the art with the invention, its principles and its practical application so that others skilled in the art may adapt and apply the invention in its numerous forms, as may be best suited to the requirements of a particular use.

With reference to the use of the word(s) "comprise" or "comprises" or "comprising" in this entire specification (including the claims below), it is noted that unless the context requires otherwise, those words are used on the basis and clear understanding that they are to be interpreted inclusively, rather than exclusively, and that it is intended each of those words to be so interpreted in construing this entire specification.

What is claimed is:

1. An oxidation catalyst comprising platinum and tellurium at a surface of a carbon support, tellurium constituting from about 0.02% to about 0.175% by weight of the catalyst.

2. An oxidation catalyst as set forth in claim 1 wherein the tellurium constitutes from about 0.02% to about 0.125% by weight of the catalyst.

3. An oxidation catalyst as set forth in claim 2 wherein the tellurium constitutes from about 0.02% to about 0.1% by weight of the catalyst.

4. An oxidation catalyst as set forth in claim 3 wherein the tellurium constitutes from about 0.02% to about 0.08% by weight of the catalyst.

5. An oxidation catalyst as set forth in claim 4 wherein the tellurium constitutes from about 0.04% to about 0.08% by weight of the catalyst.

6. An oxidation catalyst as set forth in claim 5 wherein the tellurium constitutes about 0.075% by weight of the catalyst.

TABLE 27

Oxidation Results for Pt/Fe catalyst (Experiment 1)

| Elapsed Time (min) | $O_2$ Flow (sccm) | feed NPMIDA (wt %) | exit NPMIDA (wt %) | feed Glyphosate (wt %) | exit Glyphosate (wt %) | feed $CH_2O$ (ppm) | exit $CH_2O$ (ppm) | feed HCOOH (ppm) | exit HCOOH (ppm) |
|---|---|---|---|---|---|---|---|---|---|
| 77.0 | 300.0 | 3.49 | 0.82 | 1.51 | 3.47 | 1098.9 | 2083.9 | 2118.7 | 4385.0 |
| 147.0 | 300.0 | 3.49 | 0.52 | 1.51 | 3.23 | 1098.9 | 1674.8 | 2118.7 | 4653.9 |
| 205.0 | 300.0 | 3.49 | 0.80 | 1.51 | 3.49 | 1098.9 | 2195.2 | 2118.7 | 4206.5 |
| 280.0 | 300.0 | 3.49 | 0.84 | 1.51 | 3.48 | 1098.9 | 2215.4 | 2118.7 | 4167.7 |
| 1212.0 | 300.0 | 3.49 | 1.07 | 1.51 | 3.40 | 1098.9 | 2344.2 | 2118.7 | 3991.1 |
| 1378.0 | 300.0 | 3.49 | 1.18 | 1.51 | 3.40 | 1098.9 | 2361.3 | 2118.7 | 3973.1 |
| 1447.0 | 300.0 | 3.49 | 1.17 | 1.51 | 3.38 | 1098.9 | 2347.3 | 2118.7 | 4008.4 |
| 1618.0 | 300.0 | 3.49 | 1.26 | 1.51 | 3.35 | 1098.9 | 2323.1 | 2118.7 | 3985.8 |
| 1795.0 | 300.0 | 3.49 | 1.35 | 1.51 | 3.31 | 1098.9 | 2356.2 | 2118.7 | 3896.4 |
| 2683.0 | 300.0 | 3.49 | 1.39 | 1.51 | 3.27 | 1098.9 | 2316.2 | 2118.7 | 3861.0 |
| 2789.0 | 300.0 | 3.49 | 1.45 | 1.51 | 3.30 | 1098.9 | 2353.9 | 2118.7 | 3871.0 |
| 2885.0 | 300.0 | 3.49 | 1.53 | 1.51 | 3.25 | 1098.9 | 2310.5 | 2118.7 | 3796.1 |
| 3071.0 | 450.0 | 3.49 | 0.98 | 1.51 | 3.43 | 1098.9 | 2520.4 | 2118.7 | 3935.2 |
| 3180.0 | 700.0 | 3.49 | 0.88 | 1.51 | 3.55 | 1098.9 | 2653.0 | 2118.7 | 4086.1 |

TABLE 28

Oxidation Results for Pt/Fe and Pt/Fe/Te catalysts (Experiment 2)

| Elapsed Time (min) | $O_2$ Flow (sccm) | feed NPMIDA (wt %) | exit NPMIDA (wt %) | feed Glyphosate (wt %) | exit Glyphosate (wt %) | feed $CH_2O$ (ppm) | exit $CH_2O$ (ppm) | feed HCOOH (ppm) | exit HCOOH (ppm) |
|---|---|---|---|---|---|---|---|---|---|
| 48.0 | 315.0 | 3.25 | 0.82 | 1.60 | 3.18 | 1222.1 | 940.17 | 2299.6 | 3757.3 |
| 156.0 | 330.0 | 3.25 | 0.75 | 1.60 | 3.15 | 1222.1 | 1087.2 | 2299.6 | 3975.6 |
| 210.0 | 365.0 | 3.25 | 0.57 | 1.60 | 3.27 | 1222.1 | 1200.9 | 2299.6 | 4114.4 |
| 281.0 | 410.0 | 3.25 | 0.46 | 1.60 | 3.39 | 1222.1 | 1306.9 | 2299.6 | 4182.9 |
| 339.0 | 410.0 | 3.25 | 0.67 | 1.60 | 3.35 | 1222.1 | 1306.5 | 2299.6 | 4191.2 |
| 626.0 | 400.0 | 3.25 | 0.92 | 1.60 | 3.30 | 1222.1 | 1385.2 | 2299.6 | 4081.0 |
| 1295.0 | 425.0 | 3.25 | 1.10 | 1.60 | 3.15 | 1222.1 | 1289.0 | 2299.6 | 3910.2 |
| 1424.0 | 450.0 | 3.25 | 1.16 | 1.60 | 3.14 | 1222.1 | 1341.6 | 2299.6 | 3951.3 |
| 1548.0 | 450.0 | 3.25 | 1.13 | 1.60 | 3.07 | 1222.1 | 1292.0 | 2299.6 | 3948.4 |
| 1648.0 | 450.0 | 3.25 | 1.16 | 1.60 | 3.17 | 1222.1 | 1264.6 | 2299.6 | 3916.0 |
| 1762.0 | 450.0 | 3.25 | 1.26 | 1.60 | 3.11 | 1222.1 | 1234.7 | 2299.6 | 3964.7 |
| 1820.0 | 500.0 | 3.25 | 1.08 | 1.60 | 3.08 | 1222.1 | 1200.8 | 2299.6 | 4065.8 |
| 2749.0 | 500.0 | 3.25 | 1.78 | 1.60 | 2.76 | 1222.1 | 1079.1 | 2299.6 | 3927.5 |
| 2857.0 | 500.0 | 3.25 | 1.92 | 1.60 | 2.75 | 1222.1 | 1065.1 | 2299.6 | 3926.3 |
| 2986.0 | 500.0 | 3.25 | 1.69 | 1.60 | 2.68 | 1222.1 | 1031.1 | 2299.6 | 3910.7 |
| 3118.0 | 500.0 | 3.25 | 1.81 | 1.60 | 2.64 | 1222.1 | 1009.7 | 2299.6 | 3892.2 |

7. An oxidation catalyst as set forth in claim 1 wherein the platinum constitutes from about 0.5% to about 20% by weight of the catalyst.

8. An oxidation catalyst as set forth in claim 7 wherein the platinum constitutes from about 3% to about 7.5% by weight of the catalyst.

9. An oxidation catalyst as set forth in claim 7 wherein the catalyst further comprises a promoter metal selected from the group consisting of iron, bismuth, tin, cadmium, magnesium, manganese, nickel, aluminum, cobalt, lead, titanium, antimony, selenium, rhenium, zinc, cerium, zirconium, germanium and mixtures thereof.

10. An oxidation catalyst as set forth in claim 9 wherein the promoter metal is iron.

11. An oxidation catalyst as set forth in claim 10 wherein iron constitutes from about 0.1% to about 1.5% by weight of the catalyst.

12. An oxidation catalyst as set forth in claim 11 wherein iron constitutes from about 0.25% to about 1% by weight of the catalyst.

13. An oxidation catalyst as set forth in claim 11 wherein the tellurium constitutes from about 0.02% to about 0.125% by weight of the catalyst.

14. An oxidation catalyst as set forth in claim 11 wherein platinum constitutes from about 3% to about 7.5% by weight of the catalyst, tellurium constitutes from about 0.02% to about 0.1% by weight of the catalyst and iron constitutes from about 0.25% to about 1% by weight of the catalyst.

15. An oxidation catalyst as set forth in claim 14 wherein the platinum constitutes about 5% by weight of the catalyst, tellurium constitutes about 0.075% by weight of the catalyst and iron constitutes about 0.5% by weight of the catalyst.

16. An oxidation catalyst comprising a noble metal and at least two promoter metals at a surface of a carbon support wherein:
one of the promoter metals is tellurium and constitutes from about 0.02% to about 0.175% by weight of the catalyst; and
the other promoter metal is selected from the group consisting of iron, bismuth, tin, cadmium, magnesium, manganese, nickel, aluminum, cobalt, lead, titanium, antimony, selenium, rhenium, zinc, cerium, zirconium and germanium.

17. An oxidation catalyst as set forth in claim 16 wherein the tellurium constitutes from about 0.02% to about 0.125% by weight of the catalyst.

18. An oxidation catalyst as set forth in claim 17 wherein the tellurium constitutes from about 0.02% to about 0.1% by weight of the catalyst.

19. An oxidation catalyst as set forth in claim 18 wherein the tellurium constitutes from about 0.02% to about 0.08% by weight of the catalyst.

20. An oxidation catalyst as set forth in claim 19 wherein the tellurium constitutes from about 0.04% to about 0.08% by weight of the catalyst.

21. An oxidation catalyst as set forth in claim 20 wherein the tellurium constitutes about 0.075% by weight of the catalyst.

22. An oxidation catalyst as set forth in claim 16 wherein the tellurium constitutes at least about 0.05% by weight of the catalyst.

23. An oxidation catalyst as set forth in claim 16 wherein the tellurium constitutes about 0.1% by weight of the catalyst.

24. An oxidation catalyst as set forth in claim 16 wherein the tellurium constitutes about 0.125% by weight of the catalyst.

25. An oxidation catalyst as set forth in claim 16 wherein the catalyst comprises two promoter metals and the other promoter metal is iron.

26. An oxidation catalyst as set forth in claim 25 wherein the iron constitutes from about 0.1% to about 1.5% by weight of the catalyst.

27. An oxidation catalyst as set forth in claim 26 wherein the iron constitutes from about 0.25% to about 1% by weight of the catalyst.

28. An oxidation catalyst as set forth in claim 25 wherein the noble metal is selected from the group consisting of platinum, palladium, ruthenium, rhodium, iridium, silver, osmium and gold.

29. An oxidation catalyst as set forth in claim 28 wherein the noble metal is platinum.

30. An oxidation catalyst as set forth in claim 29 wherein the platinum constitutes from about 0.5% to about 20% by weight of the catalyst.

31. An oxidation catalyst as set forth in claim 30 wherein the platinum constitutes from about 3% to about 7.5% by weight of the catalyst.

32. A process for preparing a tellurium-promoted noble metal oxidation catalyst, the process comprising:
combining an oxidation catalyst precursor and a source of tellurium in a liquid medium to form an oxidation catalyst precursor slurry, the oxidation catalyst precursor comprising a noble metal at a surface of a carbon support and the catalyst precursor slurry containing dissolved oxygen and having a temperature no greater than about 50° C.; and
depositing tellurium on a surface of the oxidation catalyst precursor.

33. A process as set forth in claim 32 wherein the temperature of the catalyst precursor slurry is no greater than about 40° C.

34. A process as set forth in claim 32 wherein the temperature of the catalyst precursor slurry is no greater than about 30° C.

35. A process as set forth in claim 32 wherein the process further comprises introducing an oxygen-containing gas into the catalyst precursor slurry.

36. A process as set forth in claim 35 wherein the liquid medium comprises water.

37. A process as set forth in claim 36 wherein the liquid medium comprises an aqueous solution comprising formaldehyde.

38. A process as set forth in claim 36 wherein the liquid medium comprises an aqueous solution comprising formic acid.

39. A process as set forth in claim 35 wherein the catalyst precursor slurry is maintained at a pressure of less than about 90 psig during introduction of the oxygen-containing gas.

40. A process as set forth in claim 35 wherein the oxidation catalyst precursor comprises a noble metal selected from the group consisting of platinum, palladium, ruthenium, rhodium, iridium, silver, osmium and gold.

41. A process as set forth in claim 40 wherein the noble metal is platinum.

42. A process as set forth in claim 41 wherein the oxidation catalyst precursor further comprises a promoter metal selected from the group consisting of iron, bismuth, tin, cadmium, magnesium, manganese, nickel, aluminum, cobalt, lead, titanium, antimony, selenium, rhenium, zinc, cerium, zirconium and germanium.

43. A process as set forth in claim 42 wherein the promoter metal is iron.

44. A process as set forth in claim 43 wherein iron constitutes from about 0.1% to about 1.5% by weight of the catalyst precursor.

45. A process as set forth in claim 43 wherein iron constitutes from about 0.25% to about 1% by weight of the catalyst precursor.

46. A process as set forth in claim 35 wherein the catalyst precursor comprises a used catalyst.

47. A process as set forth in claim 35 wherein the dissolved oxygen concentration in the catalyst precursor slurry is maintained near the saturation concentration during oxidative deposition of tellurium on the surface of the oxidation catalyst precursor.

48. A process as set forth in claim 35 wherein the temperature of the catalyst precursor slurry during introduction of the oxygen-containing gas is no greater than about 40° C.

49. A process as set forth in claim 35 wherein the temperature of the catalyst precursor slurry during introduction of the oxygen-containing gas is no greater than about 30° C.

50. A process as set forth in claim 35 wherein the source of tellurium combined with the oxidation catalyst precursor in the oxidation catalyst precursor slurry is selected from the group consisting of tellurium dioxide, tellurium tetrachloride and telluric acid.

51. A process as set forth in claim 35 wherein tellurium is preferentially deposited on the surface of the oxidation catalyst precursor such that at least about 75% of the deposited tellurium atoms are associated with or bound to metals at the surface of the catalyst precursor.

52. A process as set forth in claim 35 wherein the concentration of any chelating agent capable of forming coordination compounds with tellurium in said catalyst precursor slurry is sufficiently low so as to not inhibit substantially quantitative delivery of tellurium to the surface of the catalyst precursor.

53. A process as set forth in claim 52 wherein said catalyst precursor slurry is devoid of any chelating agent capable of binding tellurium.

54. A process for preparing a tellurium-promoted noble metal oxidation catalyst, the process comprising:
contacting an oxidation catalyst precursor, a source of tellurium and $Fe_2O_3$ in a liquid medium to deposit tellurium on a surface of the catalyst precursor, the oxidation catalyst precursor comprising a noble metal at a surface of a carbon support.

55. A process as set forth in claim 54 wherein the source of tellurium comprises tellurium dioxide.

56. A process as set forth in claim 54 wherein the liquid medium comprises an aqueous solution comprising formaldehyde.

57. A process as set forth in claim 54 wherein the liquid medium comprises an aqueous solution comprising formic acid.

58. A process as set forth in claim 54 wherein the oxidation catalyst precursor comprises a noble metal selected from the group consisting of platinum, palladium, ruthenium, rhodium, iridium, silver, osmium and gold.

59. A process as set forth in claim 58 wherein the noble metal is platinum.

60. A process as set forth in claim 54 wherein the oxidation catalyst precursor further comprises a promoter metal selected from the group consisting of iron, bismuth, tin, cadmium, magnesium, manganese, nickel, aluminum, cobalt, lead, titanium, antimony, selenium, rhenium, zinc, cerium, zirconium and germanium.

61. A process as set forth in claim 60 wherein the promoter metal is iron.

62. A process as set forth in claim 61 wherein iron constitutes from about 0.1% to about 1.5% by weight of the oxidation catalyst precursor.

63. A process as set forth in claim 62 wherein iron constitutes from about 0.25% to about 1% by weight of the oxidation catalyst precursor.

64. A process as set forth in claim 54 wherein the oxidation catalyst precursor comprises a used catalyst.

65. A process as set forth in claim 54 wherein contacting said oxidation catalyst precursor, source of tellurium, and $Fe_2O_3$ in said liquid medium forms an oxidation catalyst precursor slurry, the process further comprising:
introducing an oxygen-containing gas into the catalyst precursor slurry wherein the temperature of the catalyst precursor slurry during introduction of the oxygen-containing gas is no greater than about 50° C.; and
depositing tellurium on a surface of the oxidation catalyst precursor.

66. A process as set forth in claim 65 wherein the concentration of any chelating agent capable of forming coordination compounds with tellurium in said catalyst precursor slurry is sufficiently low so as to not inhibit substantially quantitative delivery of tellurium to the surface of the catalyst precursor.

67. A process as set forth in claim 66 wherein said catalyst precursor slurry is devoid of any chelating agent capable of binding tellurium.

68. A process for oxidizing a substrate selected from the group consisting of N-(phosphonomethyl)iminodiacetic acid or a salt thereof, formaldehyde and formic acid, the process comprising:
contacting the substrate with an oxidizing agent in the presence of an oxidation catalyst comprising a noble metal and tellurium at a surface of a carbon support, tellurium constituting from about 0.02% to about 0.175% by weight of the catalyst.

69. A process as set forth in claim 68 wherein the substrate is N-(phosphonomethyl)iminodiacetic acid or a salt thereof.

70. A process as set forth in claim 68 wherein tellurium constitutes from about 0.02% to about 0.125% by weight of the catalyst.

71. A process as set forth in claim 68 wherein tellurium constitutes from about 0.02% to about 0.1% by weight of the catalyst.

72. A process as set forth in claim 68 wherein tellurium constitutes from about 0.02% to about 0.08% by weight of the catalyst.

73. A process as set forth in claim 68 wherein tellurium constitutes about 0.075% by weight of the catalyst.

74. A process as set forth in claim 68 wherein the noble metal is platinum.

75. A process as set forth in claim 74 wherein platinum constitutes from about 0.5% to about 20% by weight of the catalyst.

76. A process as set forth in claim 75 wherein platinum constitutes from about 3% to about 7.5% by weight of the catalyst.

77. A process as set forth in claim 75 wherein the catalyst further comprises a promoter metal selected from the group consisting of iron, bismuth, tin, cadmium, magnesium, manganese, nickel, aluminum, cobalt, lead, titanium, antimony, selenium, rhenium, zinc, cerium, zirconium, germanium and mixtures thereof.

78. A process as set forth in claim 77 wherein the promoter metal comprises iron.

79. A process as set forth in claim 78 wherein iron constitutes from about 0.1% to about 1.5% by weight of the catalyst.

80. A process as set forth in claim 79 wherein iron constitutes from about 0.25% to about 1% by weight of the catalyst.

81. A process as set forth in claim 79 wherein tellurium constitutes from about 0.02% to about 0.125% by weight of the catalyst.

82. A process as set forth in claim 79 wherein platinum constitutes from about 3% to about 7.5% by weight of the catalyst, tellurium constitutes from about 0.02% to about 0.1% by weight of the catalyst and iron constitutes from about 0.25% to about 1% by weight of the catalyst.

83. A process as set forth in claim 82 wherein the platinum constitutes about 5% by weight of the catalyst, tellurium constitutes about 0.075% by weight of the catalyst and iron constitutes about 0.5% by weight of the catalyst.

84. A process as set forth in claim 68 wherein the tellurium constitutes from about 0.04% to about 0.08% by weight of the catalyst.

85. A process for oxidizing a substrate selected from the group consisting of N-(phosphonomethyl)iminodiacetic acid or a salt thereof, formaldehyde and formic acid, the process comprising:

contacting the substrate with an oxidizing agent in the presence of an oxidation catalyst comprising a noble metal and at least two promoter metals at a surface of a carbon support, wherein one of the promoter metals is tellurium and constitutes from about 0.02% to about 0.175% by weight of the catalyst and the other promoter metal is selected from the group consisting of iron, bismuth, tin, cadmium, magnesium, manganese, nickel, aluminum, cobalt, lead, titanium, antimony, selenium, rhenium, zinc, cerium, zirconium and germanium.

86. A process as set forth in claim 85 wherein the substrate is N-(phosphonomethyl)iminodiacetic acid or a salt thereof.

87. A process as set forth in claim 85 wherein the tellurium constitutes from about 0.02% to about 0.125% by weight of the catalyst.

88. A process as set forth in claim 87 wherein the tellurium constitutes from about 0.02% to about 0.1% by weight of the catalyst.

89. A process as set forth in claim 88 wherein the tellurium constitutes from about 0.02% to about 0.08% by weight of the catalyst.

90. An oxidation catalyst as set forth in claim 89 wherein the tellurium constitutes from about 0.04% to about 0.08% by weight of the catalyst.

91. A process as set forth in claim 85 wherein the tellurium constitutes at least about 0.05% by weight of the catalyst.

92. A process as set forth in claim 85 wherein the tellurium constitutes about 0.1% by weight of the catalyst.

93. A process as set forth in claim 85 wherein the tellurium constitutes about 0.125% by weight of the catalyst.

94. A process as set forth in claim 85 wherein the oxidation catalyst comprises two promoter metals and the other promoter metal is iron.

95. A process as set forth in claim 94 wherein iron constitutes from about 0.1% to about 1.5% by weight of the catalyst.

96. A process as set forth in claim 95 wherein iron constitutes from about 0.25% to about 1% by weight of the catalyst.

97. A process as set forth in claim 94 wherein the oxidation catalyst comprises a noble metal selected from the group consisting of platinum, palladium, ruthenium, rhodium, iridium, silver, osmium and gold.

98. A process as set forth in claim 97 wherein the noble metal is platinum.

99. A process as set forth in claim 98 wherein platinum constitutes from about 0.5% to about 20% by weight of the catalyst.

100. A process as set forth in claim 99 wherein platinum constitutes from about 3% to about 7.5% by weight of the catalyst.

* * * * *